(12) United States Patent
Ahmad et al.

(10) Patent No.: US 12,285,270 B2
(45) Date of Patent: *Apr. 29, 2025

(54) SMART WRISTBAND FOR MULTIPARAMETER PHYSIOLOGICAL MONITORING

(71) Applicant: The Access Technologies, Ottawa (CA)

(72) Inventors: Saif Ahmad, Kanata (CA); Atul Kumar Garg, Kanata (CA)

(73) Assignee: The Access Technologies, Ottawa (CA)

( * ) Notice: Subject to any disclaimer, the term of this patent is extended or adjusted under 35 U.S.C. 154(b) by 423 days.

This patent is subject to a terminal disclaimer.

(21) Appl. No.: 17/720,439

(22) Filed: Apr. 14, 2022

(65) Prior Publication Data
US 2022/0249021 A1    Aug. 11, 2022

Related U.S. Application Data

(63) Continuation-in-part of application No. 17/193,833, filed on Mar. 5, 2021, now Pat. No. 11,337,615.
(Continued)

(51) Int. Cl.
*A61B 5/01* (2006.01)
*A61B 5/00* (2006.01)
(Continued)

(52) U.S. Cl.
CPC .............. *A61B 5/681* (2013.01); *A61B 5/01* (2013.01); *A61B 5/02416* (2013.01);
(Continued)

(58) Field of Classification Search
CPC ... A61B 5/02055; A61B 5/346; A61B 5/7228; A61B 5/6831; A61B 5/0006;
(Continued)

(56) References Cited

U.S. PATENT DOCUMENTS 8,945,017 B2 *  2/2015  Venkatraman ..... A61B 5/02405
                                                600/503
9,498,161 B1 * 11/2016  Sunden ................. A61B 5/681
(Continued)

*Primary Examiner* — Rex R Holmes
(74) *Attorney, Agent, or Firm* — Quinn IP Law

(57) ABSTRACT

An ergonomically designed smart wristband for clinical-grade multiparameter monitoring is disclosed. The smart wristband incorporates multiple sensors including custom-designed reflective arterial pulse sensors, a thermopile sensor, and electrocardiogram (ECG) electrodes. When the smart wristband is worn on the wrist, the biosensors contact the skin. The smart wristband may tether wirelessly to a mobile or any other computing device to continuously acquire and stream information like arterial pulse waveform and temperature data. Algorithms running on the computing device or onboard microprocessor analyze the acquired data to report parameters like blood pressure, body temperature, respiration, and blood oxygen. The device can also operate in a fully-standalone mode to accomplish continuous multiparameter physiological monitoring, analysis, and reporting. Whenever the user touches an electrode on the device with a finger of the other hand, an ECG signal is additionally acquired for monitoring parameters such as heart rate and heart rate variability.

27 Claims, 19 Drawing Sheets

Related U.S. Application Data

(60) Provisional application No. 62/986,199, filed on Mar. 6, 2020.

(51) Int. Cl.
*A61B 5/024* (2006.01)
*A61B 5/332* (2021.01)
*G16H 15/00* (2018.01)

(52) U.S. Cl.
CPC ............ *A61B 5/332* (2021.01); *A61B 5/6824* (2013.01); *A61B 5/6831* (2013.01); *A61B 5/721* (2013.01); *G16H 15/00* (2018.01); *A61B 2562/0219* (2013.01); *A61B 2562/066* (2013.01)

(58) Field of Classification Search
CPC ....... A61B 5/7285; A61B 5/7207; A61B 5/28; A61B 5/742; A61B 5/681; A61B 5/746; A61B 2562/0271; A61B 2562/0219
See application file for complete search history.

(56) References Cited

U.S. PATENT DOCUMENTS

| | | | | |
|---|---|---|---|---|
| 10,478,099 | B2* | 11/2019 | Lor | G06F 3/011 |
| 11,337,615 | B2* | 5/2022 | Ahmad | A61B 5/746 |
| 2002/0099300 | A1* | 7/2002 | Kovtun | A61B 5/308 |
| | | | | 600/509 |
| 2014/0143064 | A1* | 5/2014 | Tran | G16H 40/67 |
| | | | | 705/14.66 |
| 2018/0098731 | A1* | 4/2018 | Yoon | A61B 5/0205 |
| 2018/0344227 | A1* | 12/2018 | Cronin | A61B 5/14551 |
| 2019/0053754 | A1* | 2/2019 | Gowda | A61B 5/7264 |
| 2020/0000351 | A1* | 1/2020 | Rauhala | A61B 5/6831 |
| 2020/0100693 | A1* | 4/2020 | Velo | G16H 50/20 |
| 2021/0059586 | A1* | 3/2021 | Marriott | A61B 5/7225 |

* cited by examiner

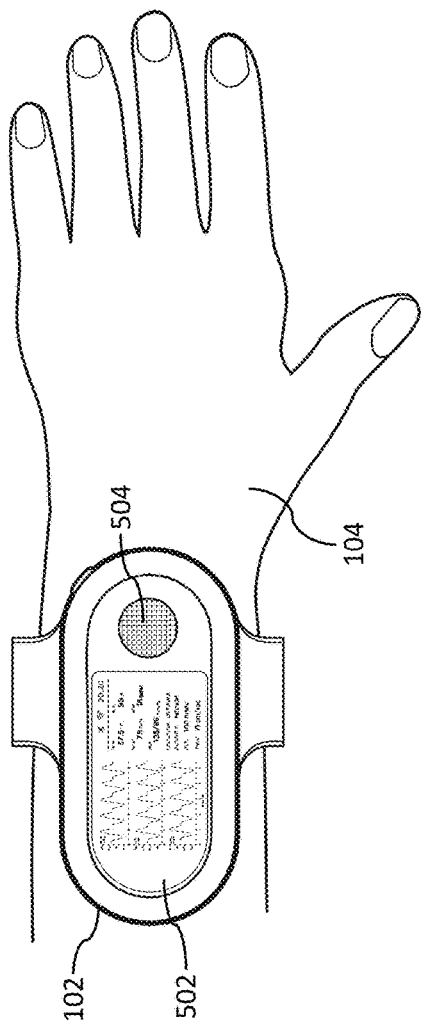
FIG. 10A
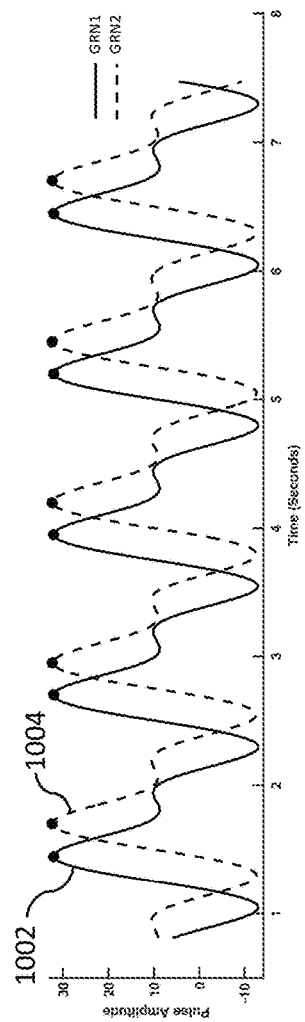
FIG. 10B
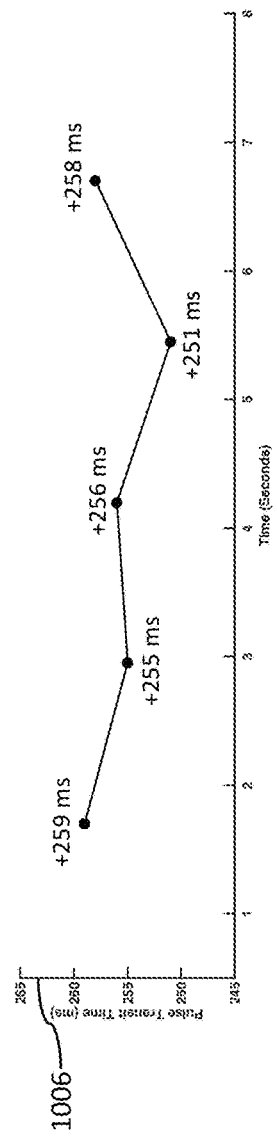

SMART WRISTBAND FOR MULTIPARAMETER PHYSIOLOGICAL MONITORING

CROSS REFERENCE TO RELATED APPLICATIONS

This application is a Continuation-in-Part of U.S. patent application Ser. No. 17/193,833, titled "Smart Wristband for Multiparameter Physiological Monitoring", which was filed on Mar. 5, 2021 and issued on May 24, 2022 as U.S. Pat. No. 11,337,615B2, and which claims priority to and benefit of U.S. Provisional Patent Application Ser. No. 62/986,199, which was filed on Mar. 6, 2020, the contents of which are hereby incorporated by reference in their entireties and for all purposes.

TECHNICAL FIELD

In general, the present invention relates to multiparameter monitoring in humans with wearable technology, and in particular to non-invasive blood pressure (NIBP), blood oxygen saturation ($SpO_2$), heart rate (HR), HR variability (HRV), respiration rate (RR), temperature, arterial pulse, and electrocardiogram (ECG) monitoring utilizing an ergonomically designed smart wristband.

BACKGROUND

The very first wrist wearable device is the mechanical movement timekeeping wristwatch that was developed in the early 19th century.

With rapid advancements in semiconductor and computing technologies, wristwatch technology has witnessed a massive growth whereby timekeeping has been accurately and efficiently accomplished via microcontrollers, digital crystals, and electronic displays. Moreover, modern day wristwatches have become increasingly smart and multi-functional such that in addition to timekeeping, they can easily perform tasks like browsing the Internet, making a telephone call, and playing audio/video media.

More recently, smartwatches or smart wristbands have been employed for non-invasively monitoring a variety of physiological phenomena and physical activity that enables users to keep track of their health. These devices are generally provided with biosensors that contact the skin of the user when worn around the wrist. In conjunction with an analog signal conditioning circuitry and a microcontroller, these biosensors acquire a variety of physiological data like arterial pulse waveform and electrocardiogram (ECG) signals, which are then analyzed to evaluate parameters like HR and blood oxygen saturation ($SpO_2$). User activity is generally monitored by analyzing the data collected by an accelerometer (ACL) provided in the device.

Smartwatches and health bands manufactured by companies like Apple, Fitbit, Samsung, Garmin, OshenWatch, and those disclosed in other prior art utilize the reflective photoplethysmography (PPG) technique to acquire arterial pulse waveform signals from the wrist. This technology generally comprises a photodiode (PD) or optical sensor along with closely located light emitting diodes (LEDs) that contact the skin of the wrist. When the LEDs glow, some light from the LEDs is absorbed by the skin while the remainder is reflected back. The PD picks up the reflected light that changes its intensity based on the changes in blood volume inside capillaries caused by the pumping of the blood by the heart. The signal picked up by the PD is conditioned and amplified using analog circuitry to characterize the arterial pulse waveform signal. The arterial pulse wave signal is then digitized via an analog to digital converter (ADC) by the microcontroller. Quite often, LEDs of different colors (or wavelengths) are utilized within the reflective PPG methodology to acquire multiple pulse waveform signals—such that each pulse waveform signal corresponds to a specific LED color or wavelength. The acquired arterial pulse waveform signals are analyzed to evaluate and monitor parameters like HR, $SpO_2$, and NIBP.

Moreover, smartwatches and health bands manufactured by companies such as Apple, Fitbit, Samsung, and those disclosed in other prior art often have the functionality to acquire an ECG signal from the wrist. To this end, a set of dry electrodes are provided on the backplate of the smartwatch while another set of dry electrodes are provided on the smartwatch face. When the user wears the smartwatch on one wrist, the backplate electrodes contact the skin of the wrist. The user then touches the smartwatch face electrodes with a finger of the other hand. This completes the ECG circuit and configures the electrodes to measure the biopotential difference between the left and right side of the body. Internally, these electrodes are connected to a differential amplifier that amplifies and conditions this biopotential difference to characterize the ECG signal. The ECG signal is then digitized via an ADC by the microcontroller. The acquired ECG signal is analyzed to evaluate and monitor parameters like HR and HRV.

Based on the ongoing discussion, it is evident that non-invasive wrist-worn physiological monitors offer the most natural, convenient, and unobtrusive method for monitoring health. However, despite all the advancements described above, wrist-worn physiological monitoring technology still seems to suffer from two major problems. These two problems are briefly described below.

The first problem is the inability of non-invasive wrist-worn monitoring technology to achieve clinical-grade accuracy and consistency for assessing various physiological parameters, especially, $SpO_2$ and NIBP. The main reason for this problem is perhaps the complex wrist physiology whereby arteries and capillaries are embedded deep inside a bony anatomical structure which hinders clean arterial pulse waveform data acquisition via the reflective PPG methodology. When acquired pulse waveform data is low-fidelity and noisy, accurate estimation of parameters like $SpO_2$ and NIBP from this data becomes problematic.

The second problem is the failure of non-invasive wrist-worn monitoring technology to conveniently and seamlessly integrate multiparameter physiological monitoring. For example, at least 6 vital signs including HR, HRV, $SpO_2$, NIBP, RR, and body temperature are of paramount importance for not only assessing overall health but also for assessing various conditions like hypertension, chronic obstructive pulmonary disease (COPD), atrial fibrillation (AF), sleep apnea, heart failure (HF), and febrile events. Yet, none of the existing technologies seem to offer accurate measurement of all these parameters in a single wrist-worn device. The main reason for this problem is perhaps the fact that wrist-worn multiparameter monitoring technology is still undergoing development whereby further advancements and enhancements are forthcoming.

Therefore, the field of non-invasive wrist-worn clinical-grade multiparameter monitoring offers several opportunities for the development of ground-breaking technologies that promise to usher in a paradigm shift in the manner in which health is monitored.

SUMMARY

The present invention is directed towards non-invasive clinical-grade multiparameter monitoring.

In one example embodiment, there is provided a non-invasive, unobtrusive, sleek, single-piece, geometric stadium-shaped wearable smart wristband related to clinical-grade continuous multiparameter physiological monitoring. The smart wristband in one example is a sealed, waterproof, and dustproof unit made from materials like thermoplastic polymers. Moreover, straps made from an elastomeric material can be provided on the device for attachment to the wrist. The smart wristband may be equipped with a microcontroller with Wi-Fi and/or Bluetooth capabilities and may utilize a rechargeable battery for power. Moreover, the smart wristband may also be provided with a 3-axes ACL that is interfaced with the microcontroller via the inter-integrated circuit (I2C) bus.

In a further example embodiment, the smart wristband backplate is provided with three custom-designed reflective PPG arterial pulse sensors. Each reflective PPG arterial pulse sensor can comprise one PD surrounded by three LEDs. The three reflective PPG arterial pulse sensors may be spread along the length of the stadium-shaped backplate which in one embodiment could be approximately 3.0" long. Each of the three custom-designed reflective PPG arterial pulse sensors can be interfaced with an analog signal conditioning and amplification circuit. Output from each of the three analog signal conditioning and amplification circuits can be connected to a separate ADC channel of the microcontroller.

Additionally, in an example embodiment, the device backplate is provided with a thermopile temperature sensor in between two of the three reflective PPG arterial pulse sensors. The thermopile temperature sensor may be interfaced with the device microcontroller via the I2C bus.

When the smart wristband is worn on the wrist, in one aspect, the length of stadium-shaped device aligns with the forearm, and the PPG and thermopile sensors contact the skin of the wrist. With this configuration, the smart wristband acquires 3-channel arterial pulse waveform data, temperature data, and ACL data, and utilizes the Wi-Fi or Bluetooth protocol to wirelessly stream this data in real-time to a mobile device (for example, smartphone, tablet, etc.) and/or a computer (for example, laptop, desktop computer, etc.) running associated software to make this data transfer possible. Additional associated software running on the mobile device and/or computer may be configured to enable the smart wristband to leverage their respective displays to enable visualization of all incoming data. Specialized algorithms, applications, and software running on the mobile device and/or the computer are capable of analyzing the incoming data to evaluate and report various parameters including cuff-less NIBP, $SpO_2$, HR, RR, temperature, and user activity. Additionally, the algorithms, applications, and software running on the mobile device and/or the computer may utilize the global positioning system (GPS) capabilities of these devices to detect and report user location. Associated software running on the mobile device and/or the computer can enable storage of all information locally and/or utilize the Wi-Fi, Bluetooth, or other protocols to transfer and store this information in the cloud and/or on other external devices. All stored information can then be transferred from one point to another, utilizing the Internet or other communication protocols, thus making remote multiparameter physiological monitoring possible.

In another embodiment, the smart wristband is designed to be fully standalone whereby it is additionally equipped with a touchscreen display on its top face, an internal memory, and a GPS module. Moreover, the fully standalone smart wristband can be provided with two ECG electrodes on its backplate and a third ECG electrode on its top face that may be interfaced with an analog differential signal amplification and conditioning circuitry. The output from the analog differential signal amplification and conditioning circuitry is capable of connecting to the fourth ADC channel of the microcontroller. When the smart wristband is worn on the wrist, the PPG sensors, the backplate ECG electrodes, and the thermopile sensor contact the skin of the wrist.

Additionally, the user touches the ECG electrode on the top face of the device with a finger of other hand. With this configuration, the fully standalone smart wristband acquires 3-channel arterial pulse waveform data, single channel ECG waveform data, temperature data, ACL data, and GPS data. Associated software running on the microcontroller can be configured to enable the touchscreen display to show incoming data in real-time. Moreover, algorithms and software running on the microcontroller are capable of processing incoming data to evaluate parameters including NIBP, $SpO_2$, HR, HRV, RR, temperature, user activity, and user location, and various results may be presented on the touchscreen display. Other information can also be presented on the screen. The fully standalone version of the smart wristband has the functionality to store all information locally in its internal memory. Moreover, the device is configured to optionally utilize the Wi-Fi, Bluetooth, or other protocols to transfer or stream information directly or from its internal memory to the cloud and/or to other external devices. Therefore, as described above, this functionality facilitates seamless remote multiparameter physiological monitoring.

In relation to the fully standalone smart wristband, it will be obvious to those skilled in the art that in case the user does not touch and hold the electrode provided on the device top face with a finger of the other hand, no ECG data will be acquired. In that case the device will only acquire and process 3-channel arterial pulse waveform data, temperature data, ACL data, and GPS data, and report associated parameters.

In one example, the smart wristband supports both manual and continuous monitoring. In manual monitoring, the user initiates a measurement that lasts a time period, such as 30 seconds, after which all data is analyzed, and results are reported. In continuous monitoring, the device automatically initiates a time period, such as a 30-second-long measurement every 15 minutes, analyzes data, and reports associated results. Again, it will be obvious to those skilled in the art that the duration of the measurements and their frequency can be easily modified as per desired monitoring needs.

In a further example embodiment, the arrangement of the three reflective PPG arterial pulse sensors along the length of the backplate of the smart wristband allows measurement of an important NIBP-related parameter called pulse transit time (PTT) between the three arterial pulse waveform signals. Since the distances between the three reflective PPG arterial pulse sensors are also known, another NIBP-related parameter called pulse wave velocity (PWV) can also be easily computed. Moreover, the amplitude of each of the three arterial pulse waveform signals is also related to the NIBP. In one example, the device is calibrated or trained by building correlations between three PTT and three pulse amplitude metrics, and NIBP measured by a standard device. Once calibrated or trained, the correlation model can be used to independently evaluate and report NIBP with clinical-grade accuracy. Preprocessing of the data from the biosensors can be undertaken using various digital signal processing (DSP) techniques such as resampling and digital filtering for removing unwanted noise and preparing the data for further analyses. This cam be followed by undertaking comprehensive data analysis utilizing specialized algorithms and software. The biosensors acquire a variety of physiological data such as arterial pulse waveform, electrocardiogram (ECG) signals, HR, HRV, $SpO_2$, NIBP, RR, body temperature, and user activity data.

In one embodiment of the smart wristband, the colors of the LEDs used in the three reflective PPG arterial pulse sensors are green (GRN1), yellow (YLW), and green (GRN2) respectively. With this configuration, utilizing different wavelengths of green (~517 nm) and yellow (~590 nm) light and their different absorption and reflection intensities by oxygenated and deoxygenated blood, two $SpO_2$ values (i. GRN1/YLW $SpO_2$ and ii. GRN2/YLW $SpO_2$) may be computed. The two computed $SpO_2$ values may be combined or fused using techniques such as arithmetic mean and weighted geometric mean to evaluate and report $SpO_2$ with clinical-grade accuracy.

In another embodiment of the smart wristband, the colors of the LEDs used in the three reflective PPG arterial pulse sensors are red (~660 nm), IR (~940 nm), and green (~517 nm) respectively. With this configuration, three $SpO_2$ values (i. red/IR $SpO_2$, ii. green/red $SpO_2$, and iii. green/IR $SpO_2$) may be computed as described above. Again, the computed $SpO_2$ values may be combined or fused using various techniques to evaluate and report $SpO_2$ with clinical-grade accuracy.

In a further aspect of the smart wristband, a HR value is calculated for each of the three arterial pulse waveform signals, resulting in three HR measurements per recording. These computed HR measurements may be combined using methods such as weighted mean to evaluate and report HR with clinical-grade accuracy. In another example, HRV information from the three arterial pulse wave signals and the ECG signal may be fused to evaluate and report HRV with clinical-grade accuracy.

In one example of the multiparameter smart wristband, respiratory sinus arrythmia (RSA) induced modulations in the three arterial pulse amplitudes, three arterial peak-to-peak intervals (PPIs), and three arterial PTTs may be utilized to estimate nine RRs, which may be followed by fusion of all calculated RRs to report RR with clinical-grade accuracy.

An arterial pulse originates at the heart and then travels to the periphery of the limbs. The described multiparameter smart wristband detects pulse arrival at three distinct locations along the wrist to measure three arterial pulses and three arterial PTTs. If the device is attached on the wrist in the correct direction, the estimated PTTs will be positive, and all related parameters will be computed accurately. However, if the device is attached on the wrist in the wrong direction, that is, it is rotated by 180 degrees, the estimated PTTs will be negative, and the computation of related parameters will suffer. In one embodiment, to overcome this limitation, the smart wristband first checks the signs of the measured PTTs. If the PTTs are found to be positive, no action is taken, and the computations proceed normally. However, if PTTs are determined to be negative, a warning may be generated to inform the user to correct the direction of the attachment of the smart wristband. As an alternative to changing the placement of the wristband, any detected negative PTT values may be transformed to positive values prior to carrying out associated computations.

In one example of the multiparameter smart wristband, the LEDs in each of the three reflective PPG arterial pulse sensors are always on. This could potentially cause the LEDs to heat up and could also lead to the LEDs associated with one PD to cause interference in other PDs—leading to loss in signal quality. To mitigate this problem, in one example, the multiparameter smart wristband may control the LEDs associated with each of the three PDs via three pulse width modulation (PWM) signals generated by three digital input/output (DIO) channels of the microcontroller. The three ADC channels interfaced with the three PDs can then be programmed to read data from a PD only when the LEDs associated with that PD are on, as determined by the duty cycles of the three PWM signals.

In one example, to enhance and standardize arterial pulse waveform signal quality and fidelity over all users, the multiparameter smart wristband utilizes the automatic gain control (AGC) technique. Here, gain of each of the three arterial pulse amplifiers may be controlled via a digital potentiometer that is also connected to the microcontroller, for example via the I2C bus. For each of the three arterial pulse waveform signals read by an ADC channel, the microcontroller may compute a peak-to-peak amplitude and accordingly alter the associated potentiometer's resistance via the I2C bus to change the corresponding amplifier's gain such that the peak-to-peak amplitude always stays above a given value, for example, 2.0 V. In a further example, the AGC technique described above may also be applied to the ECG signal to enhance and standardize its quality and fidelity over all users.

In one embodiment, the multiparameter smart wristband generates various health alerts based on the measured parameters and user activity level as determined by the ACL. For example, if the ACL data shows the subject at rest and the HR value is above 100 beats per minute (BPM), a tachycardia alert may be generated. Similarly, if the subject is resting and the NIBP value is above 140/90 mmHg, a hypertension alert may be generated.

Though this invention is described as related to a wearable multiparameter smart wristband that can be attached to a user's left or right wrist, the underlying design and principle of the invention can be extended to a wearable device that can be attached and used at any location along any of the two upper or even the two lower limbs for physiological monitoring. One example comprises the smart wristband worn and used on the left wrist. Another example comprises the device worn and used on upper the right arm. Yet another example comprises the smart wristband worn and used on the left ankle. It will be appreciated that the multiparameter smart wristband could be a smartwatch or any other similar wearable.

BRIEF DESCRIPTION OF THE DRAWINGS

FIGS. 10A-10B illustrate that when the multiparameter smart wristband is attached to the wrist in the correct direction, PTT values are positive.

DETAILED DESCRIPTION

Figure 1:
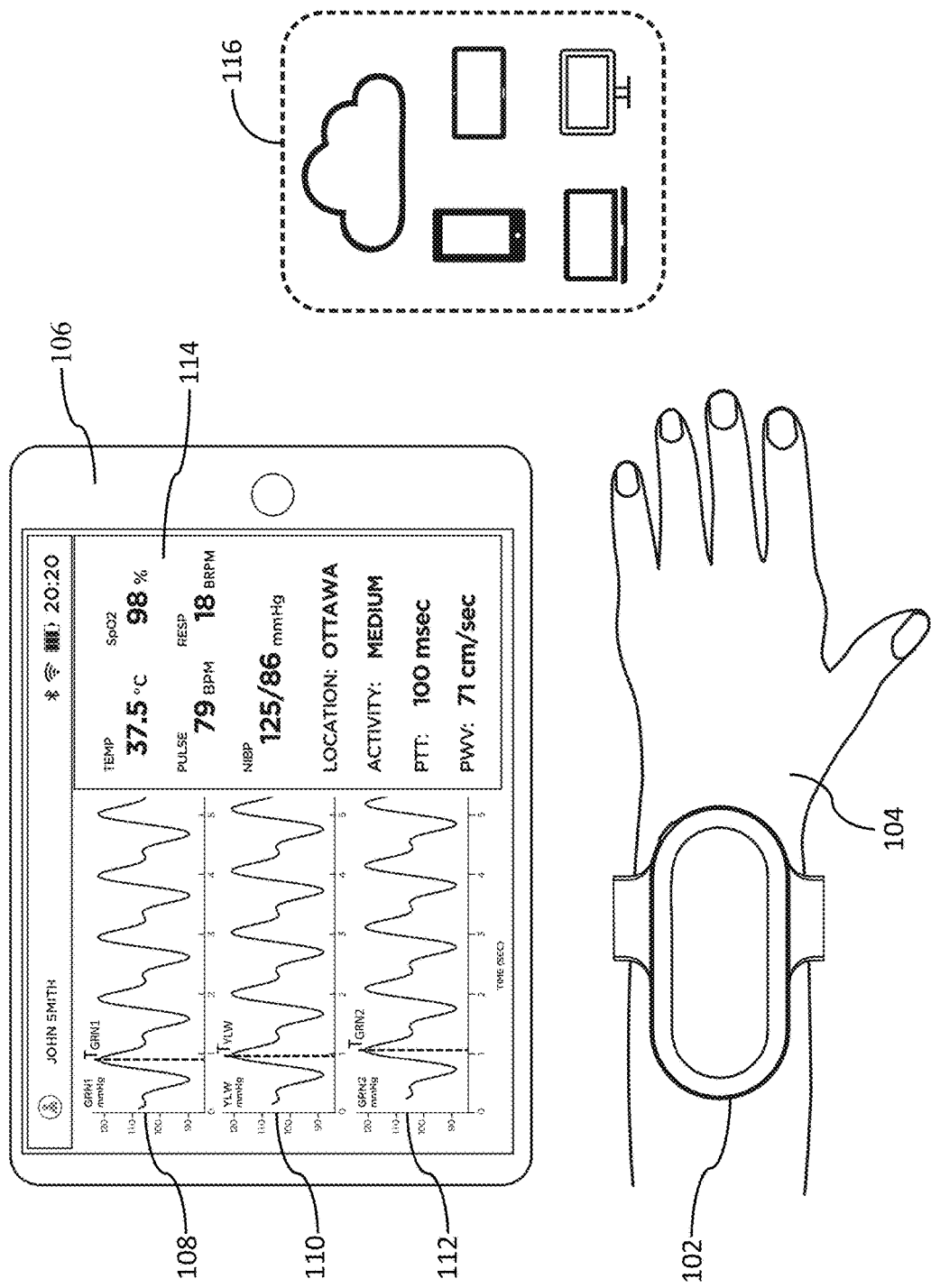
FIG. 1 illustrates the multiparameter smart wristband worn by a user on the left hand and tethered wirelessly to a tablet for monitoring data along with other external devices to which monitored data is transferred.

A preferred embodiment of the present invention will be set forth in detail with reference to the drawings, in which like reference numerals refer to like elements or method steps throughout.

FIG. 1 illustrates one embodiment of the multiparameter smart wristband worn by a user on the left hand and tethered wirelessly to a tablet for monitoring data along with other external devices to which monitored data is transferred. In this example, the smart wristband 102 is worn by the user on the left hand 104 resulting in the contact of the biosensors on the device backplate (not shown) with the skin of the wrist. The smart wristband 102 runs embedded software and communicates wirelessly with a tablet 106 running a dedicated application to accomplish real-time data acquisition and streaming to the tablet 106 via protocols such as Wi-Fi and Bluetooth. The data transferred by the smart wristband 102 to the tablet 106 includes 3-channel arterial pulse waveform signals 108, 110, 112 acquired and streamed at a sampling rate of 100 Hz each utilizing three reflective PPG arterial pulse sensors (not shown) provided on the backplate of the smart wristband 102, ACL data acquired and streamed at a sampling rate of 10 Hz utilizing an ACL sensor (not shown) provided inside the smart wristband 102, and temperature data acquired and streamed at a sampling rate of 1.0 Hz utilizing a thermopile sensor (not shown) provided on the backplate of the smart wristband 102. The dedicated application running on the tablet 106 simultaneously acquires GPS data at a sampling rate of 1.0 Hz utilizing the GPS capabilities of the tablet 106. In this example, all acquired data is analyzed by the dedicated application running on the tablet 106 to report parameters such as NIBP, SpO$_2$, HR, RR, temperature, location, activity, PTT, and PVW 114. In this embodiment of the smart wristband, the dedicated application running on the tablet 106 is capable of transferring all monitored data to other external devices 116, such as the cloud, smartphones, and computers, thus enabling seamless remote physiological monitoring. It will be obvious to those skilled in the art that the tablet 106 can be easily replaced by other similar computing devices such as a smartphone, a laptop, and a desktop computer without affecting the overall functionality of the exemplary monitoring system. Moreover, the data sampling frequencies mentioned in the description represent only one example and can be changed as per desired monitoring requirements. Operation of the smart wristband 102 is described in further detail below, with an exemplary application shown in FIG. 19.

Figure 2B:
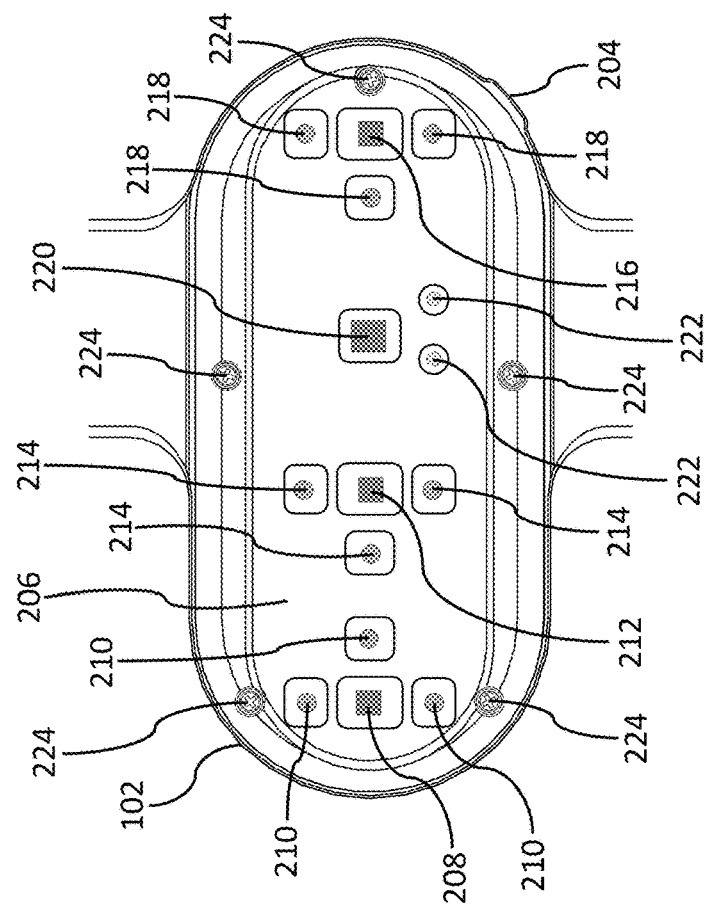
FIGS. 2A-2B illustrate the multiparameter smart wristband with its top face, power button, and backplate that incorporates reflective PPG arterial pulse sensors and thermopile sensor.
Figure 2A:
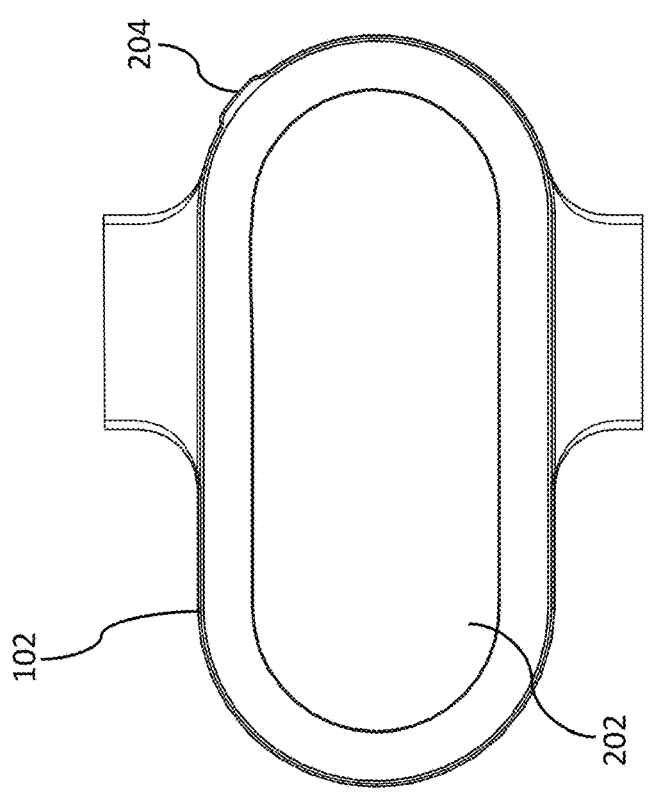

FIGS. 2A-2B illustrate an example of the multiparameter smart wristband with its top face, power button, and backplate that incorporates reflective PPG arterial pulse sensors and a thermopile sensor. In this embodiment, the smart wristband 102 comprises a flat top face 202 with no display. A power button 204 is utilized to switch the smart wristband 102 on and off. When the power button 204 is used to switch the smart wristband 102 on, an LED provided inside the device (not shown) turns on, the light from which is transmitted to the device's top face 202 via a light pipe (not shown) to indicate that the device is on. The backplate 206 is provided with three reflective PPG arterial pulse sensors. The first PPG arterial pulse sensor comprises a PD 208 surrounded by three LEDs 210 of a given color. Moreover, the second PPG arterial pulse sensor comprises a PD 212 surrounded by three LEDs 214 of another color. Additionally, the third PPG arterial pulse sensor comprises a PD 216 surrounded by three LEDs 218 of yet another color. The backplate 206 is also provided with a thermopile temperature sensor 220 that is placed in between the second and third PPG arterial pulse sensors. The LEDs 222 on the backplate 206 indicate the charging status of the smart wristband 102. The screws 224 are used to fasten together the backplate 206 and top face 202 of the smart wristband 102.

One skilled in the art will appreciate that variants exist in the arrangement and configuration of the components on the backplate 206. For example, the thermopile temperature sensor 220 may be located between the first and second PPG arterial pulse sensors. Similarly, two or more of the LED sets 210, 214 and 218 could have the same colour.

In one example the smart wristband 102 is in the shape of a geometric stadium of overall length 3.45", overall width 1.60", and overall thickness 0.55". Moreover, the distance between: (i) PD 208 of the first PPG arterial pulse sensor and the PD 212 of the second PPG arterial pulse sensor is 0.98", (ii) PD 212 of the second PPG arterial pulse sensor and the PD 216 of the third PPG arterial pulse sensor is 1.64", and (iii) PD 208 of the first PPG arterial pulse sensor and the PD 216 of the third PPG arterial pulse sensor is 2.62". Therefore, when the smart wristband 102 is worn on the wrist as shown in FIG. 1, the PPG arterial pulse sensors described above measure three arterial pulse waveform signals at three distinct locations along the wrist separated by distances of 0.98", 1.64", and 2.62". Since the arterial pulse wave travels from the heart to the periphery of the limbs, the above arrangement of PPG arterial pulse sensors enable acquisition of three arterial pulses with three different pulse arrival times. These different pulse arrival times enable the computation of three PTT metrics. Moreover, since the distances between each of the three PDs are known, the computation of three corresponding PWV metrics is straightforward.

One skilled in the art will appreciate that variants exist in the sizing of the smart wristband and location of the three PPG arterial pulse sensor. It is only necessary for the three separate PPG arterial pulse sensors to be spaced apart in a manner to detect three separate arterial pulses; accordingly, the exact location of the PPG arterial pulse sensors within the backplate 206 can vary. Similarly, the size and shape of the smart wristband 102 can vary. For example, while an oblong or oval shape of a geometric stadium is preferred, one skilled in the art could configure the shape as rectangular, circular or any other shape that would accommodate three separate PPG arterial pulse sensors spaced apart in a manner to detect three separate arterial pulses.

Figure 3:
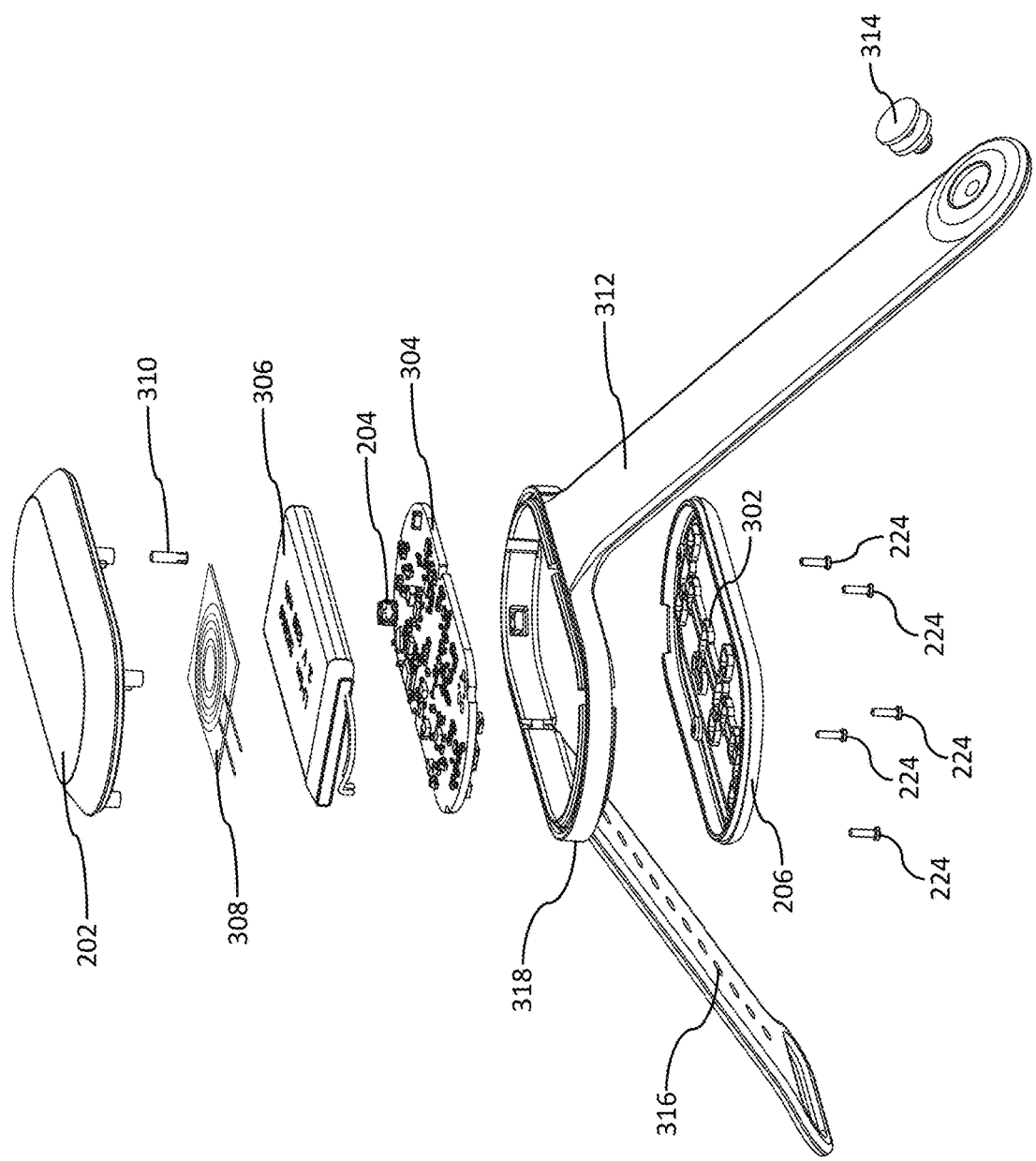
FIG. 3 illustrates an exploded view of the multiparameter smart wristband showing various components.

FIG. 3 illustrates an exploded view of the example multiparameter smart wristband showing various components. In one example embodiment, the backplate 206 comprises a light barrier boundary 302 that prevents light crosstalk between various LEDs and PDs to enable acquisition of high-quality arterial pulse waveform data. In a further example embodiment, the backplate 206 is manufactured via the industrial co-moulding process whereby the backplate material is moulded using acrylonitrile butadiene styrene (ABS) while each of the window cut-outs for the PDs 208, 212, 216, LEDs 210, 214, 218, 222, and thermopile sensor 220 is moulded using transparent acrylic. This process creates individualized transparent acrylic lenses that separately cover each LED, each PD, and the thermopile sensor. There are two advantages of the described co-moulding process. First, it fully encapsulates the LEDs 210, 214, 218, 222, PDs 208, 212, 216, and the thermopile sensor 220 to efficiently provide waterproofing and dustproofing. Secondly and most importantly, it restricts any internal light spread within a lens to that lens only, again preventing light crosstalk between various LEDs and PDs to enable acquisition of high-fidelity arterial pulse waveform data. Other methods of manufacturing may also be used to manufacture the backplate 206.

In the example embodiment shown in FIG. 3, the PDs 208, 212, 216, LEDs 210, 214, 218, 222, and thermopile sensor 220 are mounted (not shown) on a custom-designed printed circuit board (PCB) 304. The power button 204 is also mounted on the PCB 304. Other types of mountings can be contemplated by those skilled in the art.

Referring to FIG. 3, in one embodiment, the device strap 312 may be made from elastomeric rubber. The strap 312 may be manufactured as a single piece wherein a gasket 318 is integrated with the strap 312. The gasket portion 318 of the strap 312 helps to make the device waterproof and dustproof. The strap 312 may also be provided with a clasp 314 and holes 316 that enable the device to be conveniently fastened around the wrist to achieve a snug fit. Other arrangements of clasps, holes, and materials for formation of the device strap 312 may be used. For example, Velcro™ could be used for closure of the straps. In addition, while inclusion of the gasket 318 provides advantages, the gasket 318 is optional and the strap 312 may be manufactured without it. Furthermore, the strap may be formed of multiple pieces if required. While it is advantageous to manufacture the smart wristband as a sealed, waterproof, and dustproof unit, other configurations are envisioned that are not sealed, waterproof, and/or dustproof, depending upon the needs of the user. In addition, the strap could be formed of other material besides elastomeric rubber, such as nylon-like material or other suitable materials.

FIG. 3 also shows a rechargeable battery 306 provided inside the device. In one example, the device PCB 304 is provided with Qi wireless charging circuitry to which is attached a charging coil 308. With this configuration, the device battery 306 is charged utilizing the Qi wireless charging protocol. The wireless charging circuitry integrated with the PCB 304 enables the device battery to be charged wirelessly with a standard wireless charger. This enables the device enclosure to be completely sealed, simplifying the waterproofing requirement. Other forms of power sources for the device can be contemplated, such as through removable and/or replaceable batteries or through wired charging.

With reference to FIG. 3, an optional light pipe 310 is provided to carry light from the power on indication LED (not shown) provided on the PCB 304 to the top face 202 of the multiparameter smart wristband 102. Finally, the screws 224 fasten all components together.

Figure 4:
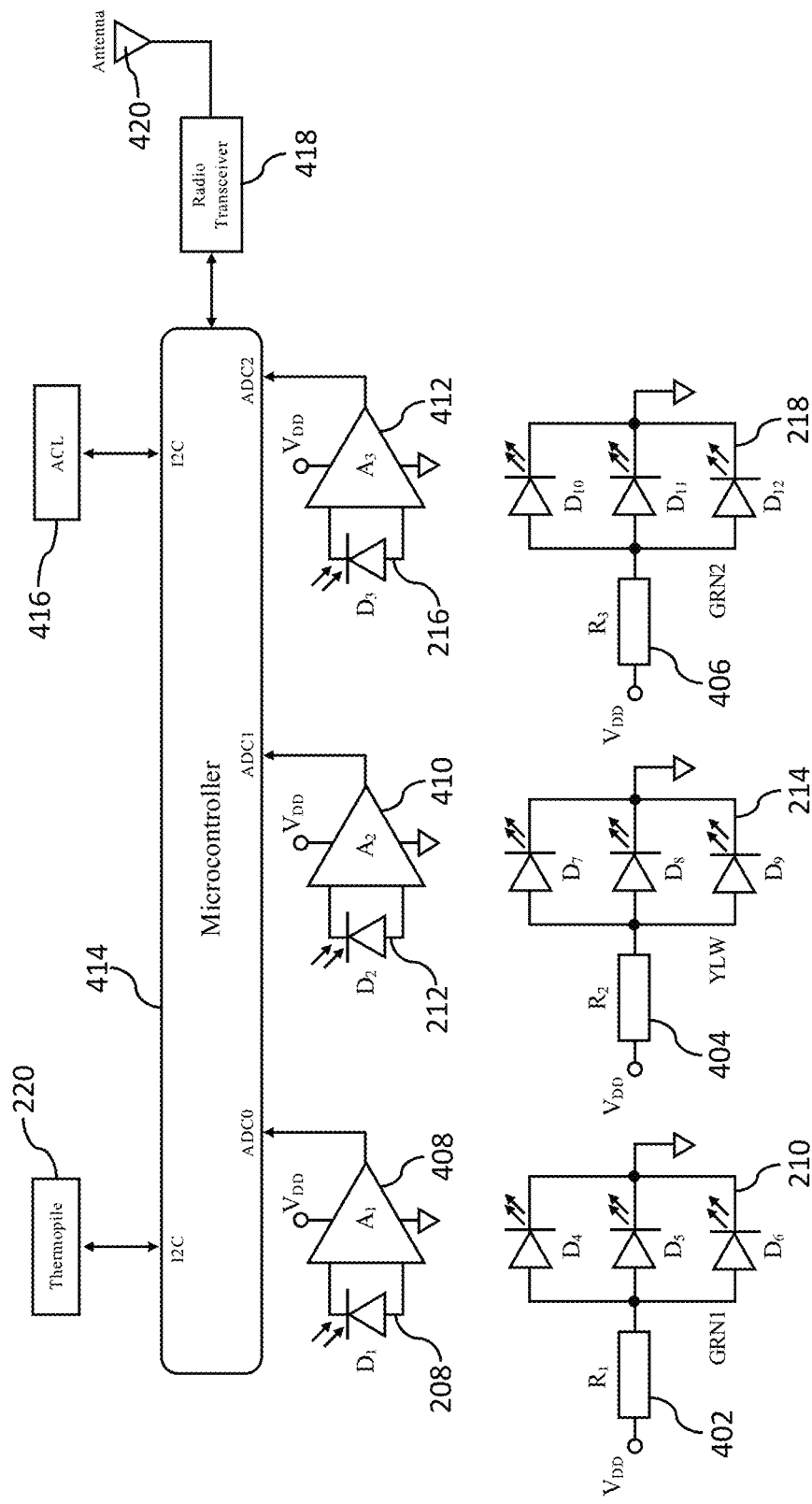
FIG. 4 illustrates an operational diagram of the multiparameter smart wristband showing several components and their various connections.

FIG. 4 illustrates an exemplary operational diagram of the multiparameter smart wristband showing several components and their various connections. The brightness of the three LED clusters 210, 214, 218 may be controlled via three resistors 402, 404, 406 respectively. The three PDs 208, 212, 216 are connected to three analog signal amplification and conditioning circuits 408, 410, 412 respectively, the outputs of which are connected to three ADC channels (ADC0, ADC1, ADC3) of the microcontroller 414. The thermopile temperature sensor 220 may be connected to the microcontroller 414 via the I2C bus. Moreover, ACL sensor 416 may also be connected to the microcontroller 414 through the I2C bus. A radio transceiver 418 along with an antenna 420 may be connected to the microcontroller 414 that enables the smart wristband to communicate wirelessly with the outside world utilizing protocols such as Wi-Fi and Bluetooth.

Referring to FIG. 1, FIG. 2B, and FIG. 4, in one embodiment, the LED cluster 210 comprises three green LEDs ($D_4$, $D_5$, $D_6$), the LED cluster 214 comprises three yellow LEDs ($D_7$, $D_8$, $D_9$), and the LED cluster 218 comprises three green LEDs ($D_{10}$, $D_{11}$, $D_{12}$). The three acquired pulse waveform signals can therefore be referred to as green 1 (GRN1) 108, yellow (YLW) 110, and green 2 (GRN2) 112 since these signals are collected by three PDs 208, 212, 216 that correspond to the green 210, yellow 214, and green 218 LED clusters. The pulse arrival time for each of the three pulse waveform signals 108, 110, 112 will be different. Therefore, it can be assumed that the time at which signal GRN1 108 peaks is $T_{GRN1}$, the time at which signal YLW 110 peaks is $T_{YLW}$, and the time at which signal GRN2 112 peaks is $T_{GRN2}$. The three PTTs can therefore be defined as follows:

$$PTT_{YG1} = T_{YLW} - T_{GRN1} \tag{1}$$

$$PTT_{G2Y} = T_{GRN2} - T_{YLW} \tag{2}$$

$$PTT_{G2G1} = T_{GRN2} - T_{GRN1} \tag{3}$$

Further, based on the distances between the three PDs 208, 212, 216 and equations (1) to (3) above, three PWVs can be defined as follows:

$$PWV_{YG1} = 0.98/PTT_{YG1} \tag{4}$$

$$PWV_{G2Y} = 1.64/PTT_{G2Y} \tag{5}$$

$$PWV_{G2G1} = 2.62/PTT_{G2G1} \tag{6}$$

Since the distances between the three PDs 208, 212, 216 are always fixed in the multiparameter smart wristband 102, the resulting measurements of the PTT and PWV metrics will be standardized across all subjects. That is, any differences observed in these metrics across various subjects will be actual differences that arise due to subject physiology alone and not due to the measurement mechanism. For example, if PTT is measured using an ECG signal and an arterial pulse waveform signal measured at the index finger, the value of the measured PTT will be dependent on the physical distance between the heart (where the ECG signal originates) and the index finger (where the pulse waveform signal is measured). This physical distance will change for every subject based on characteristics like height and built. Therefore, the PTT measured via this method will not be standardized across all subjects and differences observed across subjects will also be a function of factors such as subject height and build. Moreover, to compute PWV, the above-mentioned physical distance will have to be measured or known, making the ECG-based method of PTT measurement cumbersome. On the other hand, the design of the multiparameter smart wristband 102 offers an extremely standardized and convenient method of measuring PTT and PWV.

Referring to FIG. 1, the respective amplitudes of the GRN1 108, YLW 110, and GRN2 112 pulse waveforms can be represented by $A_{G1}$, $A_Y$, $A_{G2}$. Similarly, the respective PPIs can be represented by $PPI_{G1}$, $PPI_Y$, $PPI_{G2}$.

The PTT, PWV, and pulse amplitude information obtained from the three arterial pulse waveform signals 108, 110, and 112 can be combined using various statistical and computational techniques to evaluate NIBP. In one embodiment, the three PTT and the three pulse amplitude metrics are combined inside a multiple regression model to determine NIBP as follows:

$$NIBP = B_0 + B_1 * PTT_{YG1} + B_2 * PTT_{G2Y} + B_3 * PTT_{G2G1} + B_4 * A_{G1} + B_5 * A_Y + B_6 * A_{G2} \tag{7}$$

The multiple regression model described in equation (7) is trained utilizing simultaneous measurements from the multiparameter smart wristband 102 and a standard NIBP device on various subjects to determine constants $B_0$-$B_6$. Once trained, the linear regression model of equation (7) may be used to evaluate and report cuff-less NIBP with clinical-grade accuracy.

In another embodiment, a log product of the three PWV and the three pulse amplitude metrics are combined inside a regression model to determine cuff-less NIBP with clinical-grade accuracy as follows:

$$NIBP = B_0 + B_1 * \log(PWV_{YG1} * PWV_{G2Y} * PWV_{G2G1} * A_{G1} * A_Y * A_{G2}) \tag{8}$$

NIBP is generally reported as two numbers, namely, systolic pressure (SP) and diastolic pressure (DP), whereby the unit of measurement is mmHg. In equations (7) and (8), the NIBP term can be replaced by either SP or DP. Since SP is different in magnitude (generally 120 mmHg) than the DP (generally 80 mmHg), separate regression models (of the type shown in equations (7) and (8)) are built for SP and DP. Once calibrated, these models may be utilized to evaluate and report cuff-less SP and DP with clinical-grade accuracy.

Calibration and training may occur using a standard peripheral BP monitor on a per subject and population cohort basis. Relationship mappings between PWV and systolic/diastolic pressure may be created using various techniques like statistical linear/nonlinear regressions and artificial neural network modeling. An advantage is that the relationship mappings can also be created using an aortic/carotid BP monitor. Therefore, after calibration and training, peripheral and/or aortic/carotid BP can be reported using PTT/PWV information obtained from the acquired PPG pulse waveform data. The device may be calibrated and trained by creating relationship mappings between pulse peaks/troughs/amplitudes and standard peripheral and/or aortic/carotid BP devices.

The multiparameter smart wristband 102 may combine the three PPIs using various statistical and computational techniques to evaluate HR with clinical-grade accuracy. In one example, a non-weighted mean is used as follows:

$$HR = 60 / [(PPI_{G1} + PPI_Y + PPI_{G2})/3] \tag{9}$$

Referring to equation (9), the unit of measurement of PPIs is seconds and division of 60 by the average of PPIs results in a HR reported in BPM.

In one example, the multiparameter smart wristband 102 may utilize the RSA induced modulations in the three arterial pulse amplitudes, three PPIs, and three PTTs to estimate nine RRs in breaths per minute (BRPM). This may be followed by fusion of all calculated RRs utilizing various mathematical and computational techniques to report RR with clinical-grade accuracy. Key steps of RR computation are: (i) peak detection, (ii) peak interpolation, (iii) bandpass filtering, (iv) peak detection & respiration rate extraction, and (v) fusion of all respiration rates. In one embodiment, the nine resulting RRs are aggregated by computing their weighted mean as follows:

$$RR = \frac{\sum_{i=0}^{n-1} W_{RRi} RR_i}{\sum_{i=0}^{n-1} W_{RRi}} \tag{10}$$

In equation (10), the weights are represented by $W_{RRi}$ whereby the total number of RRs are n=9. In this manner, aggregated RR may be evaluated and reported in BRPM with clinical-grade accuracy.

In one embodiment the smart wristband 102, utilizes: (i) the ratio between GRN1 and YLW pulse waveform signals to evaluate a first $SpO_2$ value and (ii) the ratio between GRN2 and YLW pulse waveform signals to evaluate a second $SpO_2$ value. In another example, the multiparameter smart wristband 102 employs red, IR, and green LED clusters inside its three PPG arterial pulse sensors and utilizes: (i) the ratio between red and IR pulse waveform signals to evaluate a first $SpO_2$ value, (ii) the ratio between green and red pulse waveform signals to evaluate a second $SpO_2$ value, and (iii) the ratio between green and IR pulse waveform signals to evaluate a third $SpO_2$ value. The evaluated $SpO_2$ values are then fused utilizing various statistical techniques to report $SpO_2$ as a percentage with clinical-grade accuracy. The three $SpO_2$ values obtained from the red, IR, and green pulse waveform signals can be represented as $S_{RIR}$, $S_{GR}$, and $S_{GIR}$. In one example, the smart wristband 102, may use an unweighted geometric mean to aggregate these three SpO$_2$ values as follows:

$$SpO_2 = \sqrt[3]{S_{RIR} * S_{GR} * S_{GIR}} \quad (11)$$

With reference to FIG. 1 and FIGS. 2A-2B, appropriate placement of the three custom-designed reflective PPG arterial pulse sensors along the backplate 206 of the smart wristband 102 facilitates the measurement of arterial pulses at three distinct locations 208, 212, 216 along the wrist, thus reducing positional dependency of pulse measurement on the wrist and increasing the probability of collection of good quality signals at one or more locations. For example, if the quality of the first arterial pulse waveform signal 108 in not good, there is a probability that the quality of the second arterial pulse waveform signal 110 is better, and so on. The fusion of information from all three pulse waveform signals 108, 110, 112 as described above thus results in the estimation of parameters such as HR, RR, SpO$_2$, and NIBP with clinical-grade accuracy.

Figure 5:
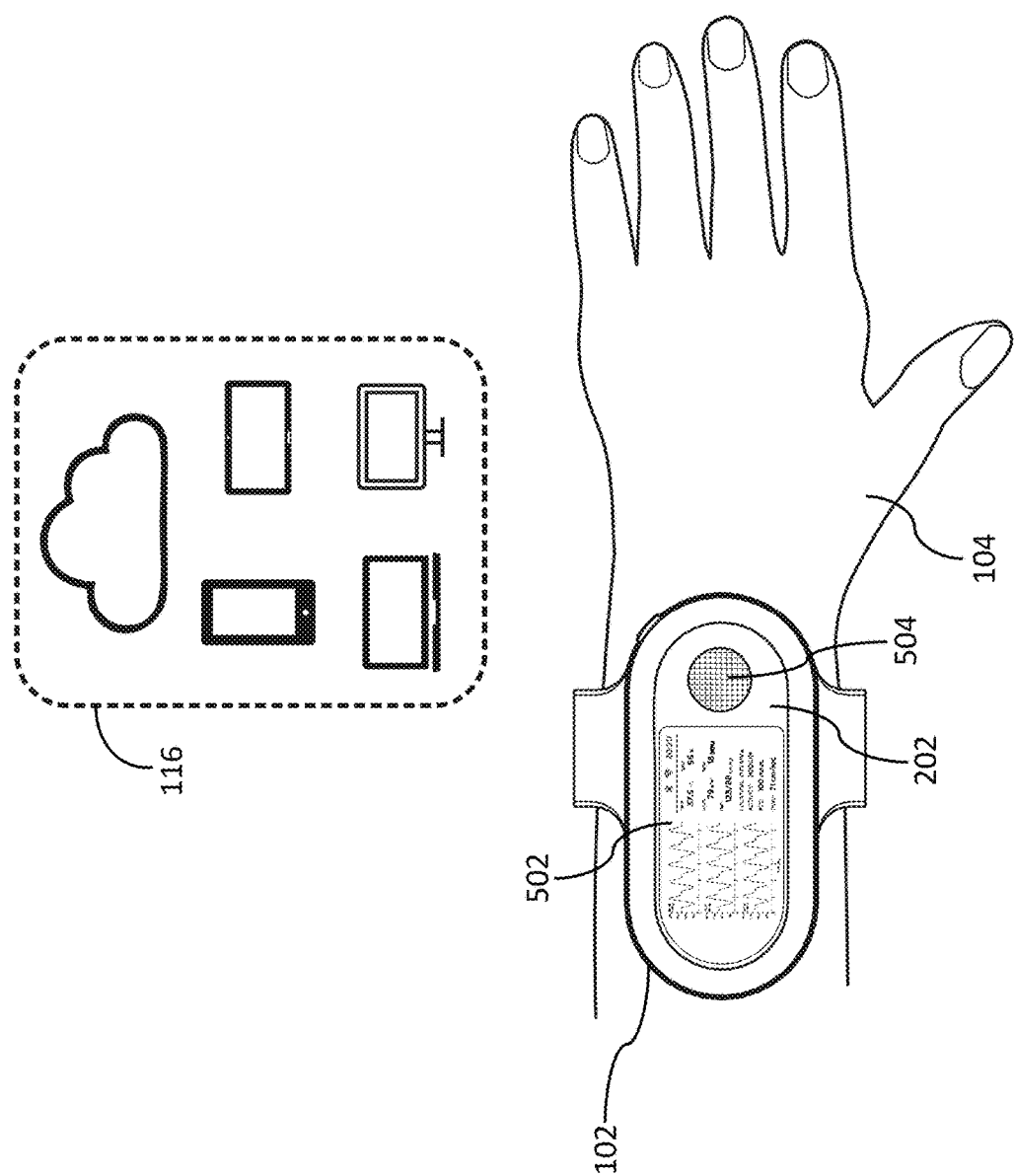
FIG. 5 illustrates a fully standalone version of the multiparameter smart wristband worn by a user on the left hand for monitoring data along with other external devices to which monitored data is wirelessly transferred.

FIG. 5 illustrates an example of a fully standalone version of the multiparameter smart wristband worn by a user on the left hand for monitoring data along with other external devices to which monitored data is optionally wirelessly transferred or streamed. In this example the multiparameter smart wristband 102 is fully standalone and is worn on the left hand 104. The multiparameter smart wristband 102 comprises a touchscreen display 502 on its top face 202 for visualizing signals and results and giving inputs to the device. The device 102 may also be provided with two ECG electrodes on its backplate (not shown) and one ECG electrode 504 on its top face 202. The fully standalone version of the multiparameter smart wristband 102 has wireless capabilities like Wi-Fi and Bluetooth so that it can conveniently (optionally) transmit all monitored data to other external devices 116. In this embodiment of the invention, all data acquisition, analysis, storage, and transmission tasks may be performed by the microcontroller (not shown) that runs dedicated embedded software.

Figure 6:
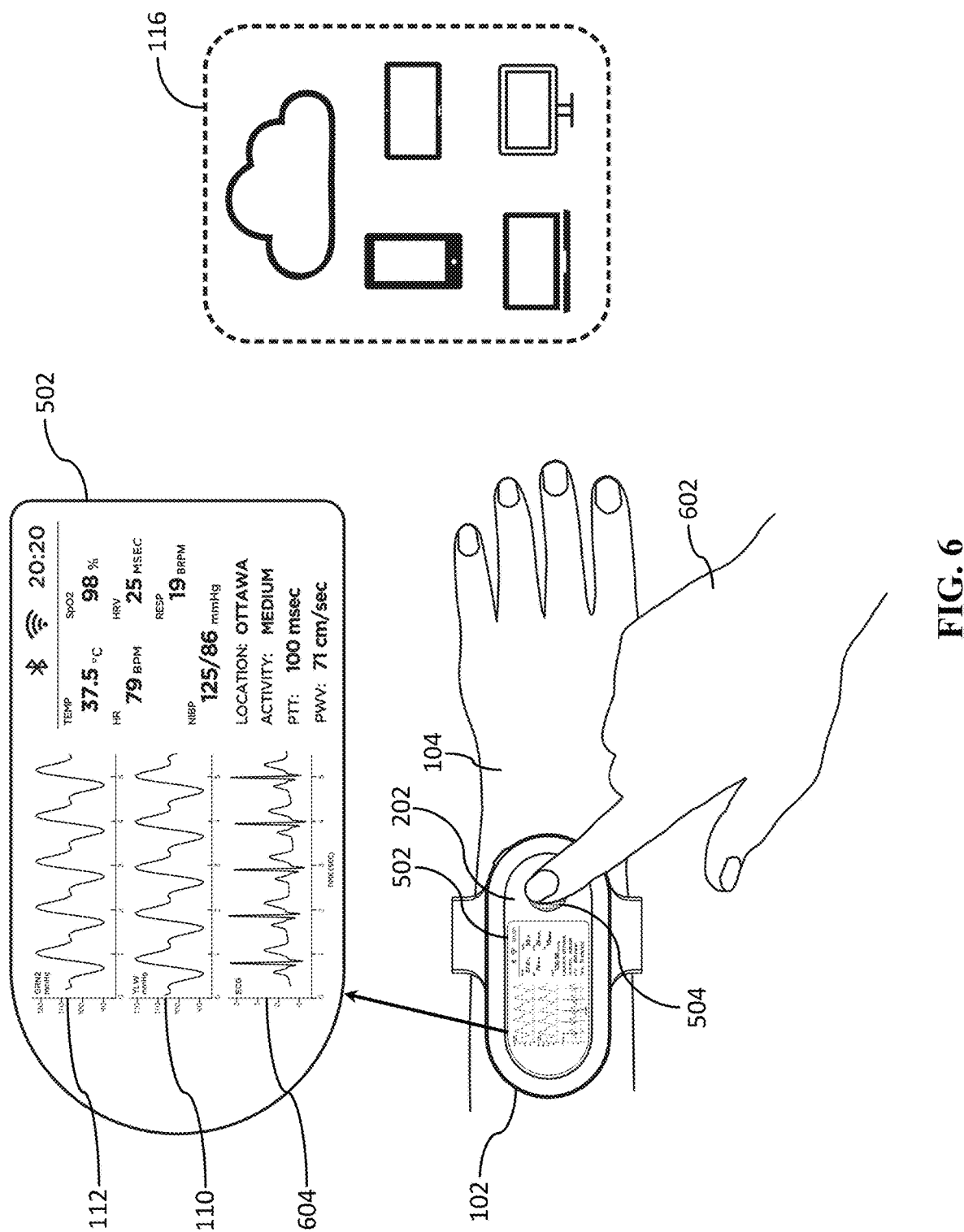
FIG. 6 illustrates a fully standalone version of the multiparameter smart wristband worn by a user on the left hand with the index finger of the right hand touching the top face ECG electrode for monitoring data that includes ECG data along with other external devices to which monitored data is wirelessly transferred.

FIG. 6 illustrates an embodiment of a fully standalone version of the multiparameter smart wristband worn by a user on the left hand with the index finger of the right hand touching the top face ECG electrode for monitoring data that includes ECG data along with other external devices to which monitored data is optionally wirelessly transferred. The device 102 is worn on the left hand 104 such that the ECG electrodes on the backplate (not shown) contact the skin. Additionally, the ECG electrode 504 provided on the front face 202 is touched by the index finger of the right hand 602 to complete the ECG circuit. With this configuration, the multiparameter smart wristband 102 additionally acquires a single channel ECG waveform signal. In FIG. 6, a zoomed version of the touchscreen display 502 is shown whereby two arterial pulse waveform signals 110, 112 and an ECG waveform signal 604 are being monitored. In one embodiment, the device microcontroller (not shown) may detect ECG R-peaks to compute and report HR and HRV metrics with clinical-grade accuracy. Again, all monitored information may be wirelessly transferred to other external devices 116. Finally, all data acquisition, analysis, storage, and transmission tasks may be handled by the microcontroller (not shown) running dedicated embedded software.

Figure 7B:
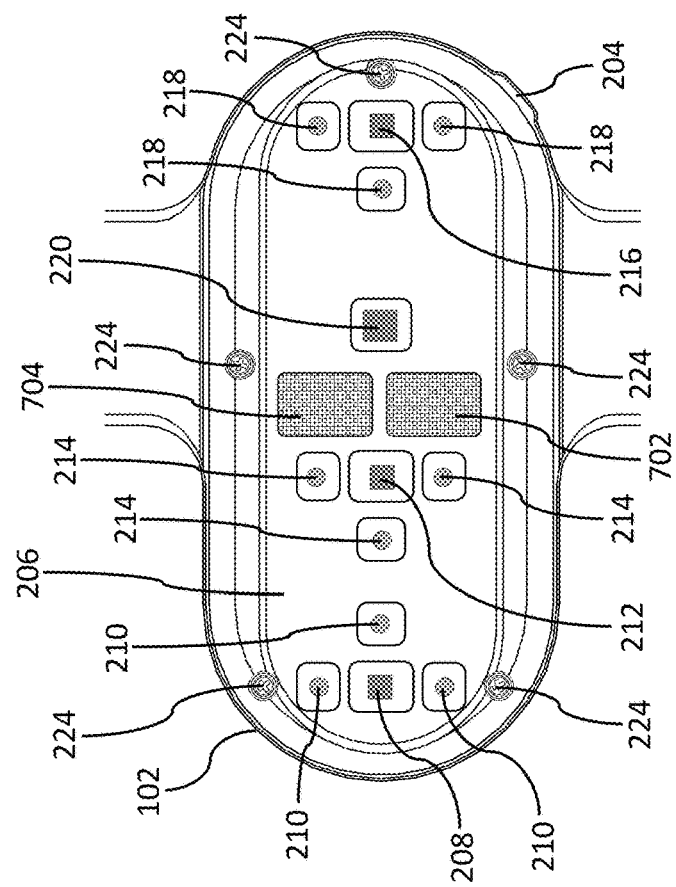
FIGS. 7A-7B illustrate a fully standalone version of the multiparameter smart wristband with its top face, power button, and backplate that incorporates reflective PPG arterial pulse sensors, thermopile sensor, and ECG electrodes.
Figure 7A:
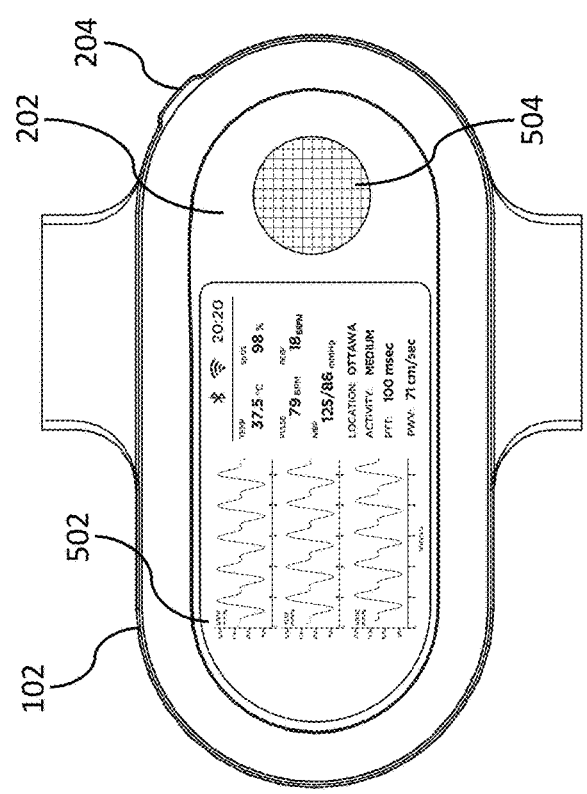

FIGS. 7A-7B illustrate an example of a fully standalone version of the multiparameter smart wristband with its top face, power button, and backplate that incorporates reflective PPG arterial pulse sensors, thermopile sensor, and ECG electrodes. In this example, the device top plate 202 is additionally provided with a touchscreen display 502 and an ECG electrode 504. Moreover, the device backplate 206 is additionally provided with two ECG electrodes 702, 704.

Figure 8:
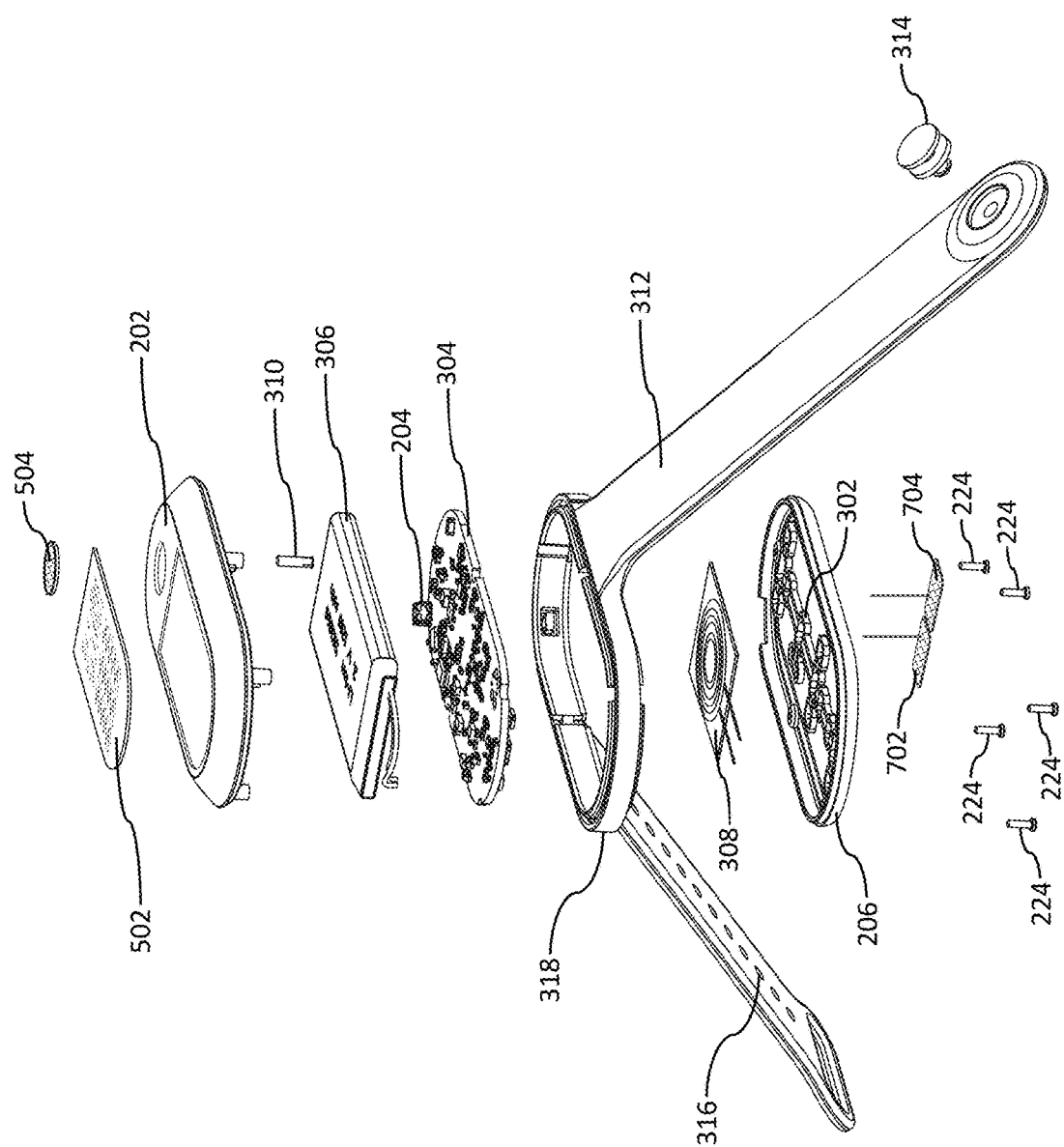
FIG. 8 illustrates an exploded view of the fully standalone version of the multiparameter smart wristband showing various components.

FIG. 8 illustrates an exploded view of the fully standalone version of the multiparameter smart wristband showing various components. In this example of the invention, the top plate 202 additionally accommodates the touchscreen display 502 and an ECG electrode 504. Moreover, the backplate 206 additionally incorporates two ECG electrodes 702, 704. In this example embodiment, due to the addition of the touchscreen display 502 on the top face 202, the charging coil 308 associated with the Qi wireless charging circuitry is provided just above the backplate 206. The charging coil 308 can be located anywhere within the multiparameter smart wristband in which it will provide charging power to the rechargeable battery 306.

Figure 9:
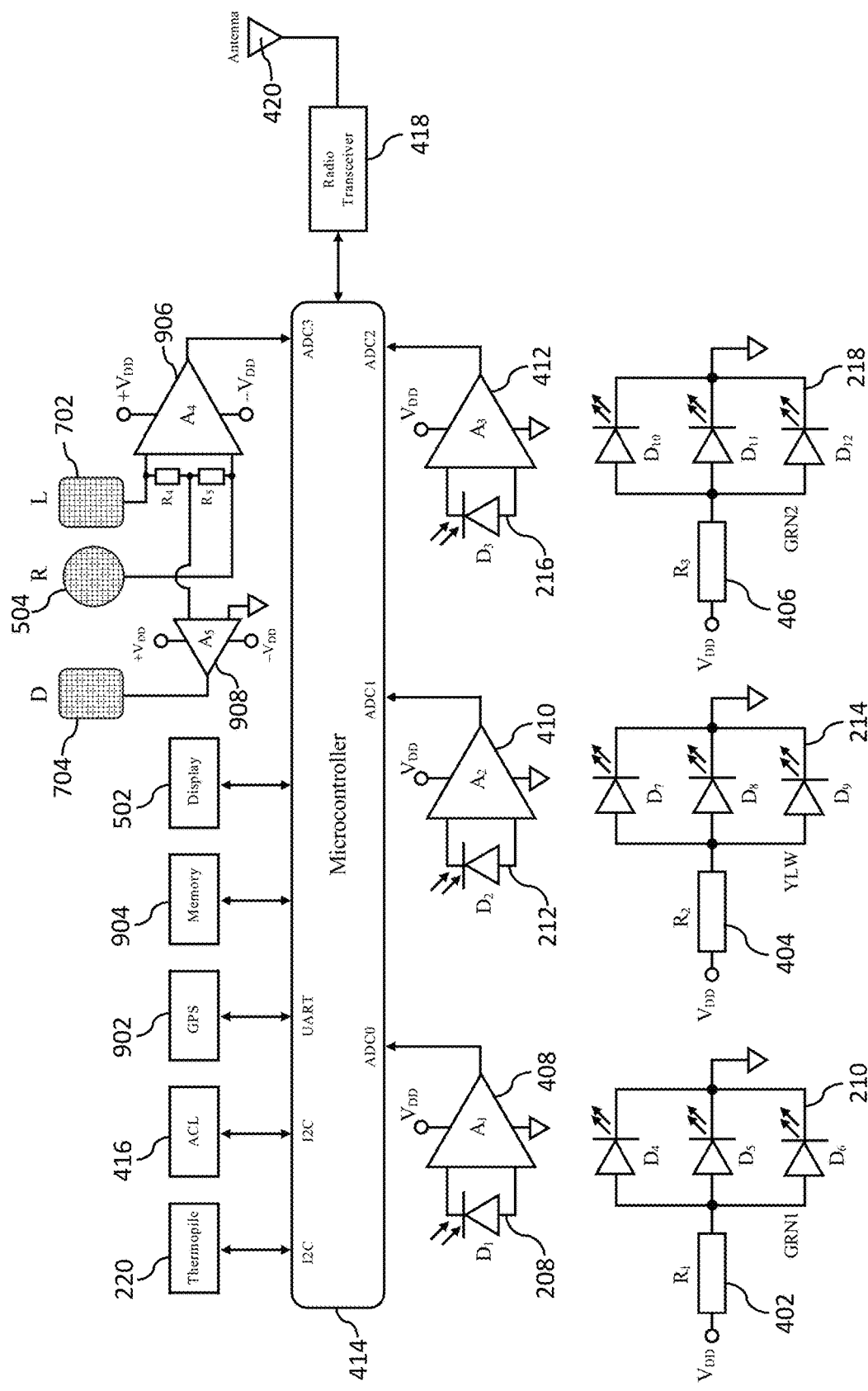
FIG. 9 illustrates an operational diagram of the fully standalone version of the multiparameter smart wristband showing several components and their various connections.

FIG. 9 illustrates an operational diagram of the fully standalone version of the multiparameter smart wristband showing several components and their various connections. Here, the microcontroller 414 may be additionally interfaced with a GPS module 902 via a UART bus, a touchscreen display 502, and a memory module 904. The first ECG electrode 702 provided on the device backplate 206 is a left-side electrode that may be connected to the first input of an analog differential amplifier 906 whereas the second ECG electrode 704 provided on the device backplate 206 is a driven electrode that may be connected to a driving amplifier 908. The ECG electrode 504 provided on the device top face 202 is a right-side electrode that may be connected to the second input of an analog differential amplifier 906. In reference to FIG. 9, the microcontroller 414 may run dedicated embedded software to independently monitor three arterial pulse waveform signals, one ECG waveform signal, user activity, and user location. Moreover, the microcontroller 414 may also run dedicated embedded software to independently analyze all data to report parameters like NIBP, SpO$_2$, HR, HRV, RR, temperature, user activity, and user location. The microcontroller 414 may also store information inside the memory module 904 as required. Finally, the microcontroller 414 transmits information wirelessly to the outside world via the radio transceiver 418 and antenna 420.

With reference to FIG. 1, FIG. 4, FIG. 6, and FIG. 9, in one embodiment, data from the ACL 416, which is synchronously collected along with the arterial pulse waveform 108, 110, 112 and ECG waveform 604 data, may be used to remove noise like motion artifacts from these signals to further enhance the accuracy of HR, HRV, RR, SpO$_2$, and NIBP estimation.

FIGS. 10A-10B illustrate that when the multiparameter smart wristband is attached to the wrist in the correct direction, PTT values are positive. With reference to FIGS. 10A-10B, the smart wristband 102 is attached on the left hand 104 in the correct and expected direction. As discussed earlier, the arterial pulse wave travels unidirectionally from the heart towards the fingers of the hand 104. Therefore, the acquired GRN1 signal 1002 leads the acquired GRN2 signal 1004 since the GRN1 PPG arterial pulse sensor (not shown) is farther away from the periphery (fingers) of the left hand 104 and the GRN2 PPG arterial pulse sensor (not shown) is closer to the periphery (fingers) of the left hand 104 underneath the device 102. In this scenario, the PTTs computed by subtracting the temporal locations of the peaks of the GRN1 signal 1002 from the temporal locations of the peaks of the GRN2 signal 1004 result in positive values 1006.

Figure 11A:
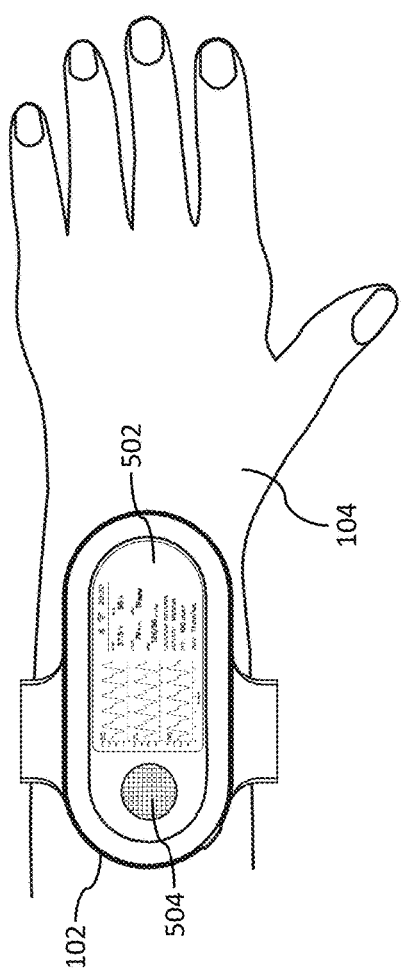
FIGS. 11A-11B illustrate that when the multiparameter smart wristband is attached to the wrist in the incorrect direction, PTT values are negative.
Figure 11B:
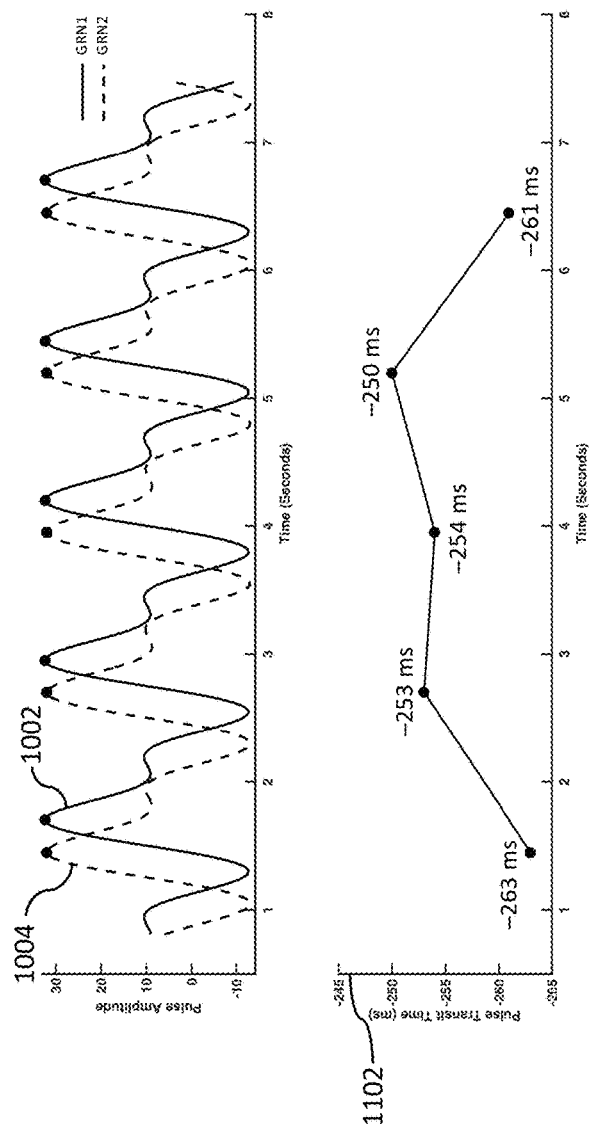

FIGS. 11A-11B illustrate that when the multiparameter smart wristband is attached to the wrist in the incorrect direction, PTT values are negative. In this scenario, the PTTs computed by subtracting the temporal locations of the peaks of the GRN1 signal 1002 from the temporal locations of the peaks of the GRN2 signal 1004 result in negative values 1102. In one embodiment, this phenomenon is utilized to automatically detect whether the user has attached the device 102 on the wrist in the correct direction or not. Moreover, when an incorrect attachment is detected and the computed PTT values are negative, they may be automatically corrected to positive values. In addition to the foregoing, or alternatively, if PTT values of less than 0 are detected, it implies that these values are negative and an alert "Smart wristband attached in the correct direction" may be generated for the user. Moreover, even if the wristband is not adjusted in the proper direction, the negative PTT values may be corrected by multiplying them by negative 1. Then the corrected PTT values may be used for further computations as needed. An example of a simplified iOS Swift code that analyzes negative PTT values 1102 to automatically detect and alert for wrong attachment of the multiparameter smart wristband 102 on the wrist and also corrects these values is presented below:

---
Smart Wristband Attachment Direction
Detection and PTT Correction
---

```
var PTT = [-263, -253, -254, -250, -261]
var negativeCount = 0
for i in 0...(PTT.count-1) {
   if (PTT[i] < 0) {
      negativeCount += 1
   }
}
if (negativeCount>0) {
   print ("Smart wristband attached in the incorrect direction")
   for i in 0...(PTT.count-1) {
      PTT[i] = -PTT[i]
   }
} else {
   print ("Smart wristband attached in the correct direction")
}
print ("Corrected PTTs =", PTT)
```

Figure 12:
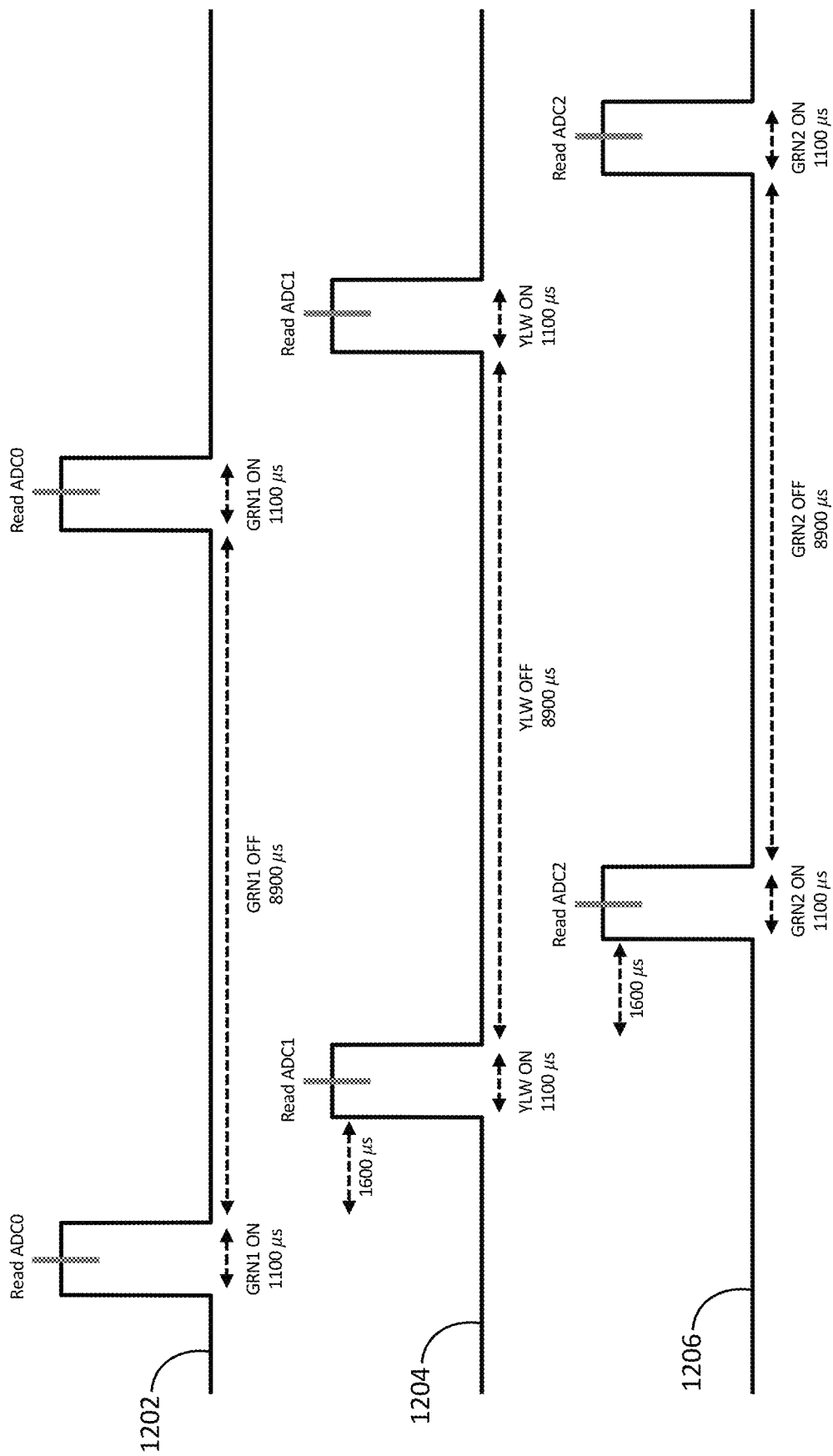
FIG. 12 illustrates the PWM technique that is utilized inside the multiparameter smart wristband for switching LEDs associated with the three PD sensors and synchronously reading data from these PD sensors.

FIG. 12 illustrates an exemplary PWM technique that may be utilized inside the multiparameter smart wristband for switching LEDs associated with the three PD sensors and synchronously reading data from these PD sensors. In this example, the three LED clusters 210, 214, 218 are switched on and off utilizing three PWM signals 1202, 1204, 1206 that are generated by three DIO channels (not shown) of the microcontroller 414. The three ADC channels (ADC0, ADC1, ADC2) of the microcontroller 414 that are interfaced with the three PDs 208, 212, 216 may be programmed to read a data sample only when the corresponding PWM signal is high. In this example, each LED cluster is on for 1100 ms and off for 8900 ms, and a data read occurs exactly at the middle of the on period. Moreover, there is a phase difference of 1600 ms between the three PWM signals 1202, 1204, 1206. This particular PWM scheme therefore results in a data sampling rate of 100 Hz each for the three acquired arterial pulse waveform signals. As discussed earlier, the described PWM technique allows that: (i) the LEDs do not heat up and (ii) the LEDs associated with one PD do not cause interference in other PDs. The described PWM technique therefore may provide the acquisition of high-quality clinical-grade arterial pulse waveform data. Other PWM techniques having different data sample rates, on/off periods and phase differences may also be used.

Figure 13:
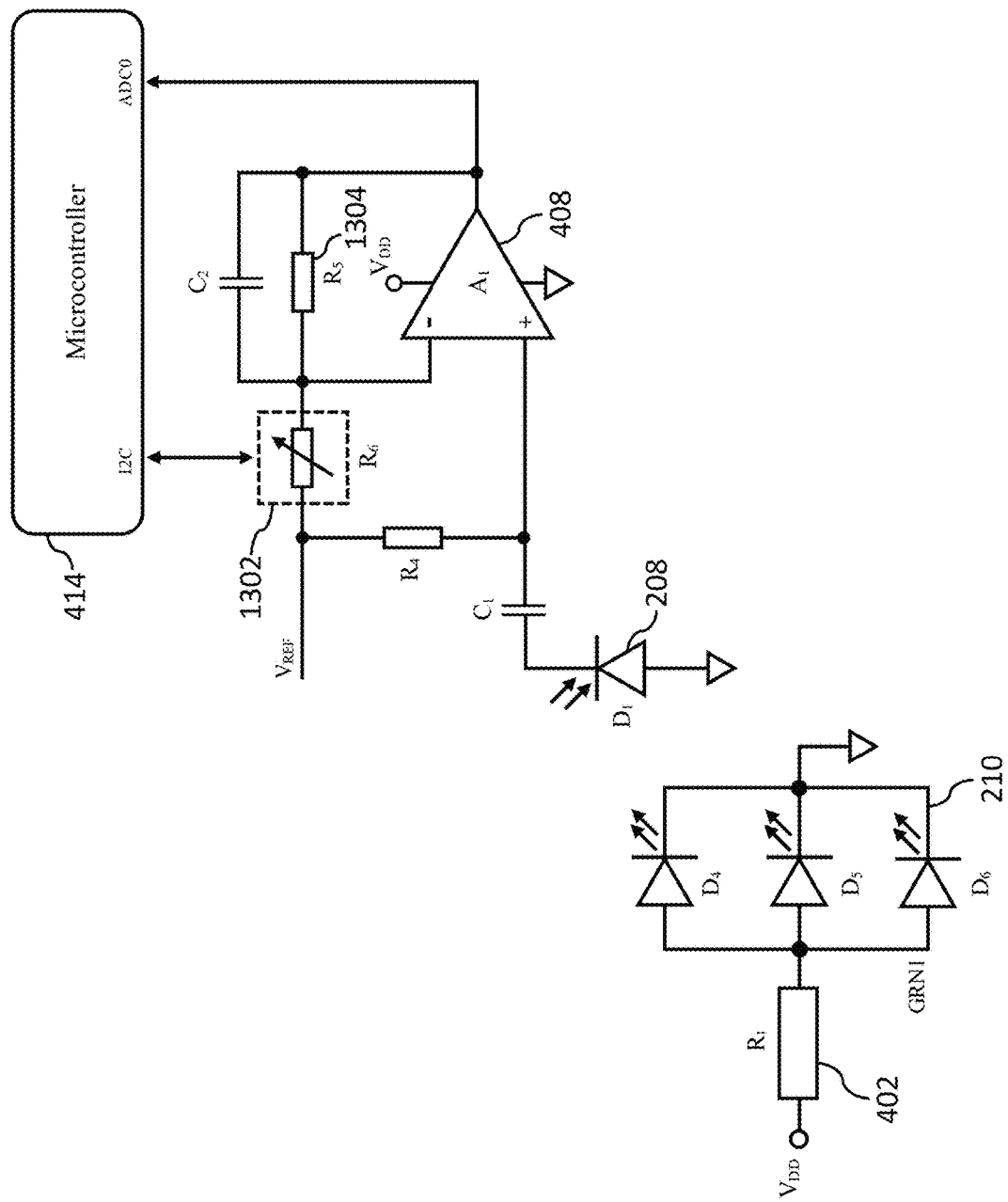
FIG. 13 illustrates an operational diagram of the AGC scheme that is utilized inside the multiparameter smart wristband to standardize arterial pulse waveform signal quality and fidelity over all users.

FIG. 13 illustrates an operational diagram of an exemplary AGC scheme that is utilized inside the multiparameter smart wristband to standardize arterial pulse waveform signal quality and fidelity over all users. In this example, the signal from the GRN1 PD 208 is amplified by the amplifier 408 after which it is fed to the ADC channel ADC0 of the microcontroller 414. The gain of the differential amplifier 408 may be controlled by an I2C potentiometer $R_6$ 1302 that is connected to an I2C port of the microcontroller 414. The non-inverting gain of the amplifier 408 may be governed by $R_5$ 1304 and the I2C potentiometer $R_6$ 1302 and represented as $G=(1+R_5/R_6)$. In one embodiment, the microcontroller 414 computes a peak-to-peak amplitude of the GRN1 arterial pulse waveform signal and automatically alters the resistance of $R_6$ 1302 via the I2C bus to change the gain of the amplifier 408 such that the peak-to-peak amplitude of the GRN1 signal always stays above 2.0 V. This AGC technique may be employed to standardize all three arterial pulse waveform signals acquired from the three PDs 208, 212, 216, resulting in the acquisition of clinical-grade high-fidelity arterial pulse waveform data from all users.

In another embodiment, three sliders may be provided on the display 114 of the tethered mobile device 106 and/or on the touchscreen display 502 of the smart wristband 102. These three sliders may be in communication with the three I2C potentiometers that control the gains of the three PD amplifiers 408, 410, 412. In one example, the user eyeballs the incoming data and then manually adjusts the gain of the three arterial pulse waveform signals using these three sliders to obtain clinical-grade high-fidelity arterial pulse waveform data.

Figure 14:
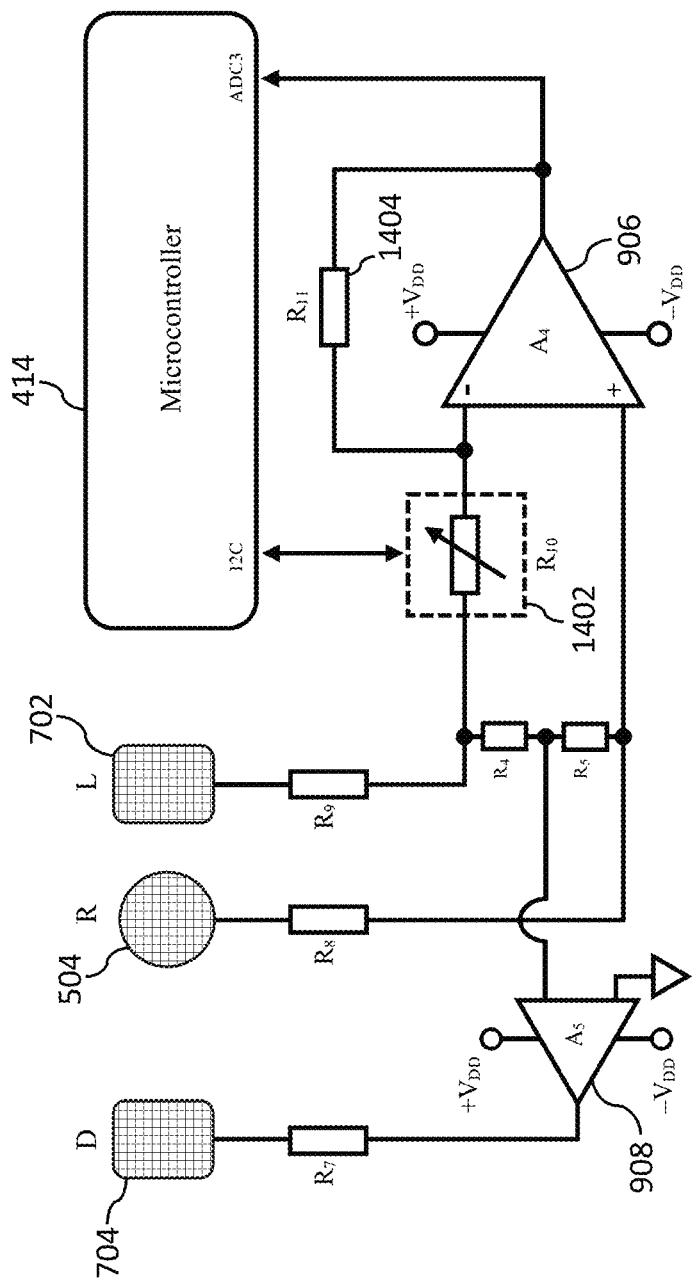
FIG. 14 illustrates an operational diagram of the AGC scheme that is utilized inside the multiparameter smart wristband to standardize ECG signal quality and fidelity over all users.

FIG. 14 illustrates an operational diagram of an example AGC scheme that is utilized inside the multiparameter smart wristband to standardize ECG signal quality and fidelity over all users. The gain control amplifier in this embodiment is an I2C potentiometer Rio 1402 that controls the gain of the ECG differential amplifier 906 in conjunction with Ru 1404. Again, the gain may be controlled automatically via the microcontroller 414 and/or manually via a user interface (UI) slider (as described above for arterial pulse waveform data) to obtain high-fidelity ECG signals for all users.

Figure 15:
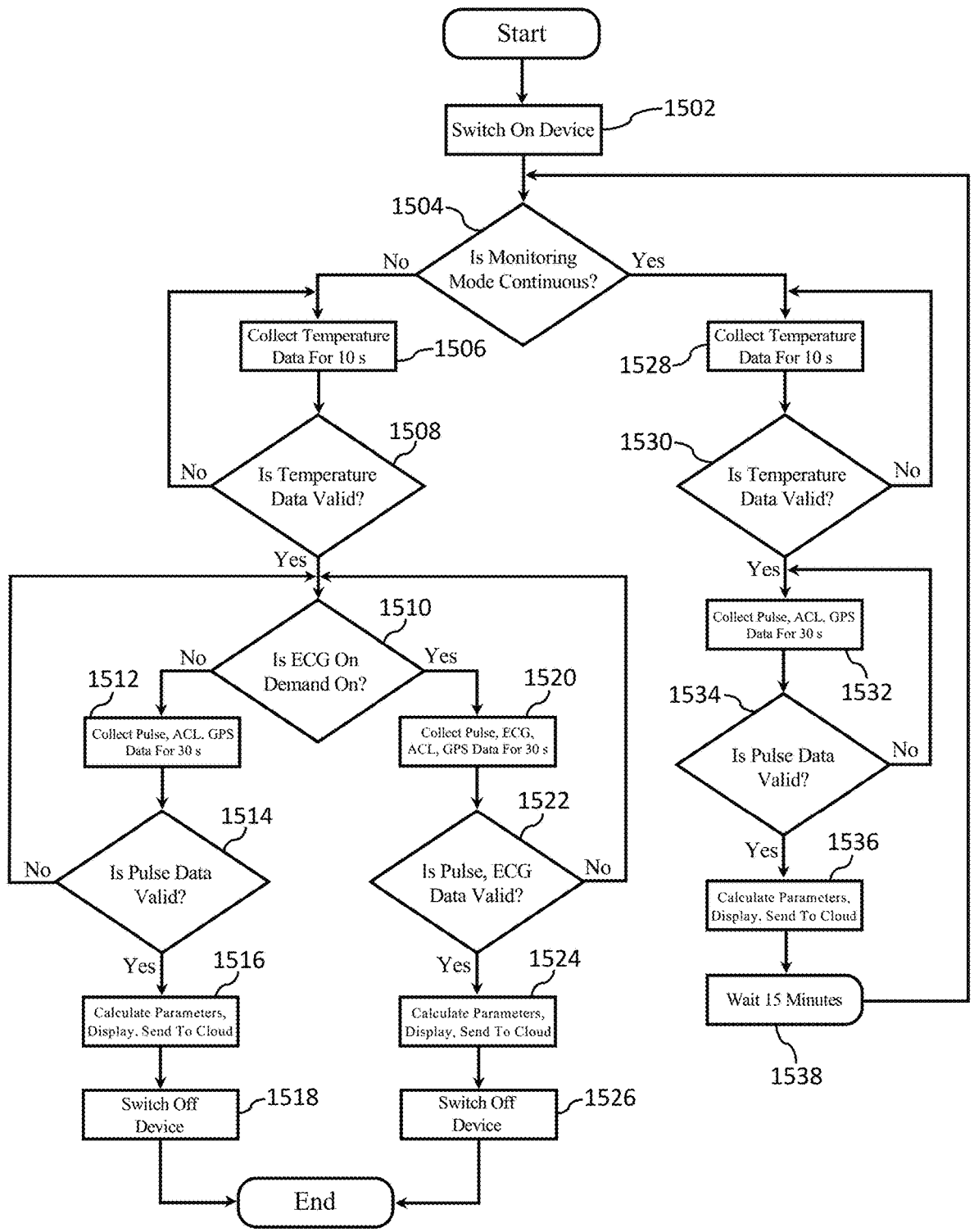
FIG. 15 illustrates a flowchart depicting the method of manual and continuous monitoring accomplished by the multiparameter smart wristband.

FIG. 15 illustrates an exemplary flowchart depicting the method of manual and continuous monitoring accomplished by the multiparameter smart wristband. The device is switched on at block 1502. At block 1504, if the monitoring mode is not continuous, then the program flow goes to block 1506 where temperature data is collected using the thermopile sensor 220 for 10 seconds. Then block 1508 checks whether the temperature data collected is valid or not and demands recollection of the temperature data via block 1506 until valid temperature data is collected. If block 1508 determines that the collected temperature data is valid, the program flow proceeds to block 1510 that checks whether ECG on demand is on or off. The ECG on demand block 1510 essentially checks whether the user is touching the ECG electrode 504 on the device top face 202 with a finger of the other hand without which ECG data acquisition cannot be accomplished. If at block 1510, ECG on demand at is on, then all data including ECG data is collected for 30 seconds or other time period at block 1520. Block 1522 then checks if collected data is valid—if not valid, program flow goes back to the ECG on demand block 1510, otherwise program flow goes to block 1524 that analyzes data, calculates and displays parameters, and optionally sends information to other external devices 116. Once a manual monitoring session is completed, block 1526 switches off the device. If ECG on demand at block 1510 is off, the program flow proceeds in a similar manner through blocks 1512, 1514, 1516, 1518, without ECG data acquisition. At block 1504, if the monitoring mode is continuous, then the program flow proceeds in a similar manner through blocks 1528, 1530, 1532, 1534, 1536 without ECG data acquisition. The block 1538 instructs the program to pause for 15 minutes after which the flow goes back to block 1504. If block 1504 maintains the monitoring mode as continuous, data is automatically collected, analyzed, displayed, and transmitted every 15 minutes.

Figure 16:
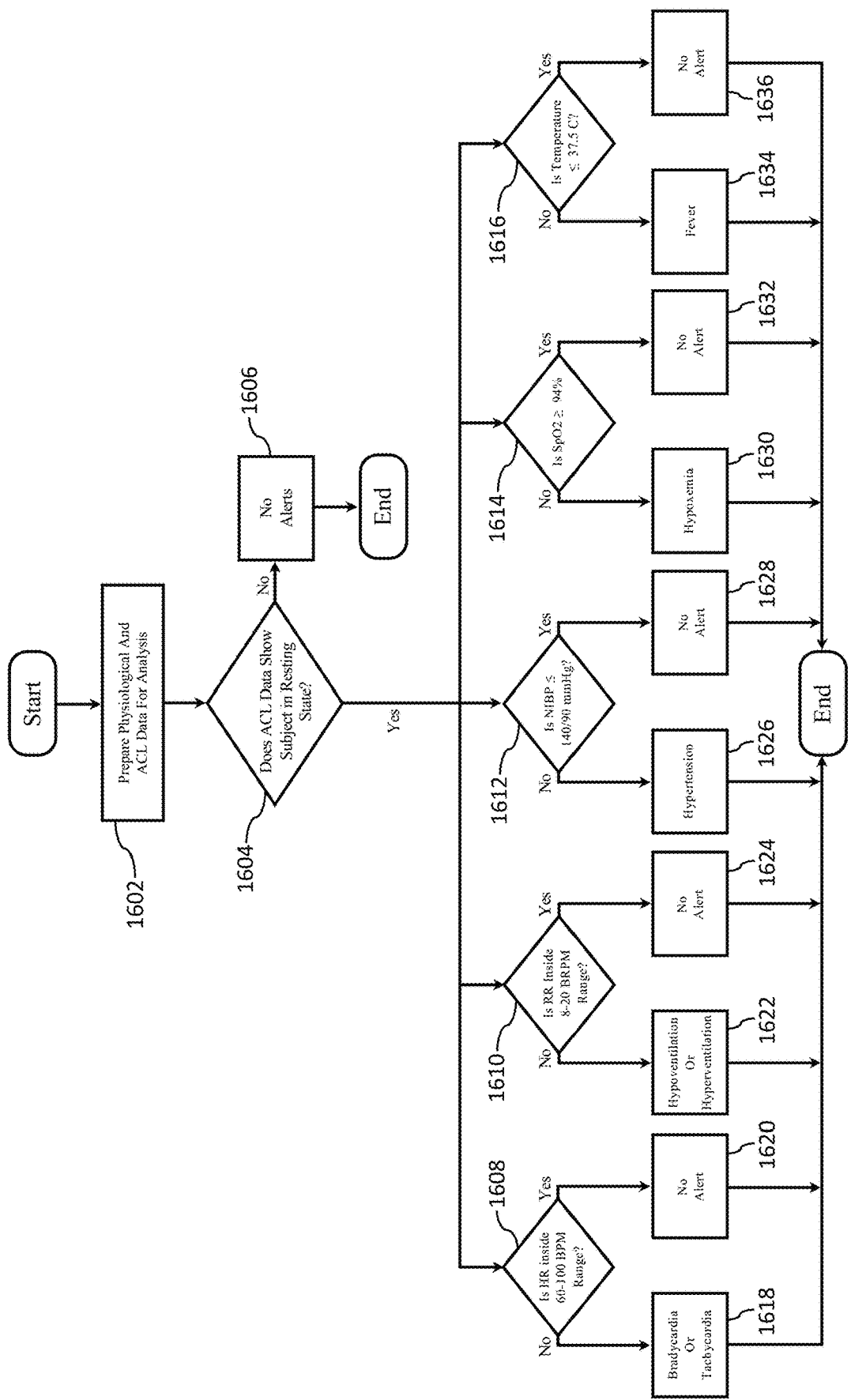
FIG. 16 illustrates a flowchart depicting the generation of various health alerts by the multiparameter smart wristband.

FIG. 16 illustrates an example flowchart depicting the generation of various health alerts by the multiparameter smart wristband. At block 1602, the program prepares physiological and ACL data for analysis. Most normal ranges of physiological parameters are defined for the resting state. Therefore, at block 1604 the program utilizes the ACL information to detect if the subject is at rest or not. If block 1604 detects that the subject is not at rest, no alerts are generated as defined by block 1606. If block 1604 determines that the subject is at rest, the program flow goes to blocks 1608, 1610, 1612, 1614, 1616 that determine whether various physiological parameters are within their clinically specified normal ranges or not. If the physiological parameters are within the desired ranges, then no alerts are generated as described by blocks 1620, 1624, 1628, 1632, 1636. Conversely, if the physiological parameters are outside the desired ranges, then alerts are generated as described by blocks 1618, 1622, 1626, 1630, 1634. For example, if the resting HR is outside the 60-100 BPM range as defined by block 1608, then a bradycardia or tachycardia alert is generated as described by block 1618.

Figure 17:
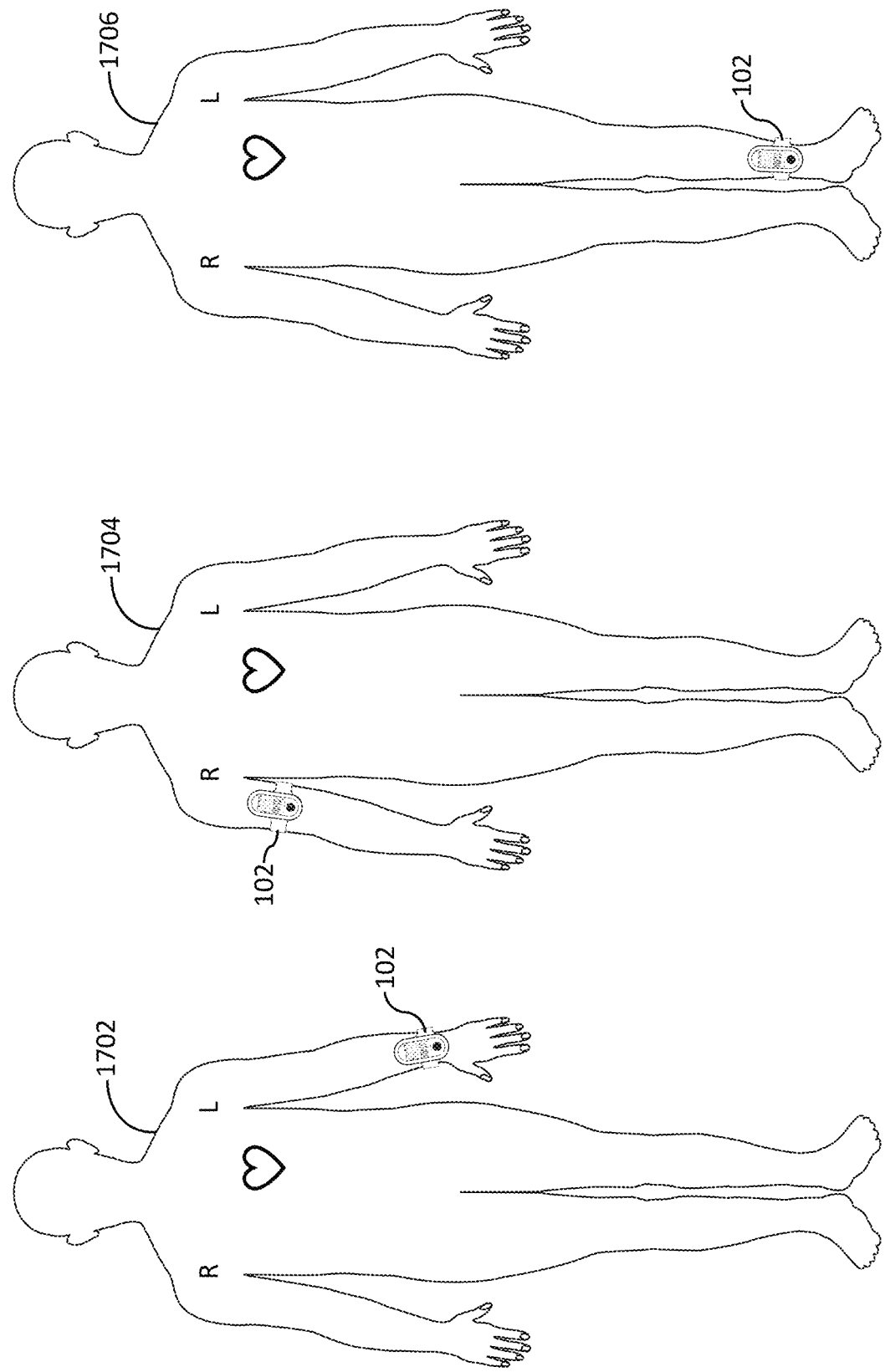
FIG. 17 illustrates examples of various locations on the human body where wearables employing the underlying design and principle of the multiparameter smart wristband can be attached to undertake monitoring.

FIG. 17 illustrates examples of various locations on the human body where wearables employing the underlying design and principle of the multiparameter smart wristband can be attached to undertake monitoring. As illustrated in 1702, the multiparameter smart wristband 102 can be worn around the left wrist for monitoring data. As illustrated in 1704, the multiparameter smart wristband 102 can be worn around the right upper arm for monitoring data. Finally, as illustrated in 1706, the multiparameter smart wristband 102 can be worn around the left ankle for monitoring data. These examples demonstrate that the disclosed multiparameter smart wristband 102 and/or similar wearable devices can be attached at various locations along the 4 limbs to accomplish manual or continuous multiparameter physiological monitoring.

Figure 18B:
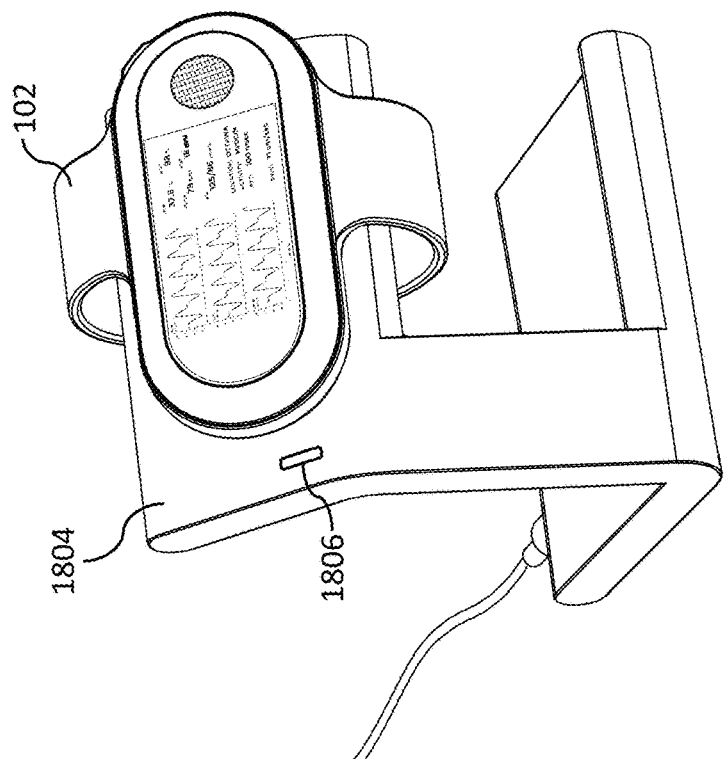
FIGS. 18A-18B illustrate the multiparameter smart wristband and the fully standalone version of the multiparameter smart wristband being charged on two different kinds of wireless charging units.
Figure 18A:
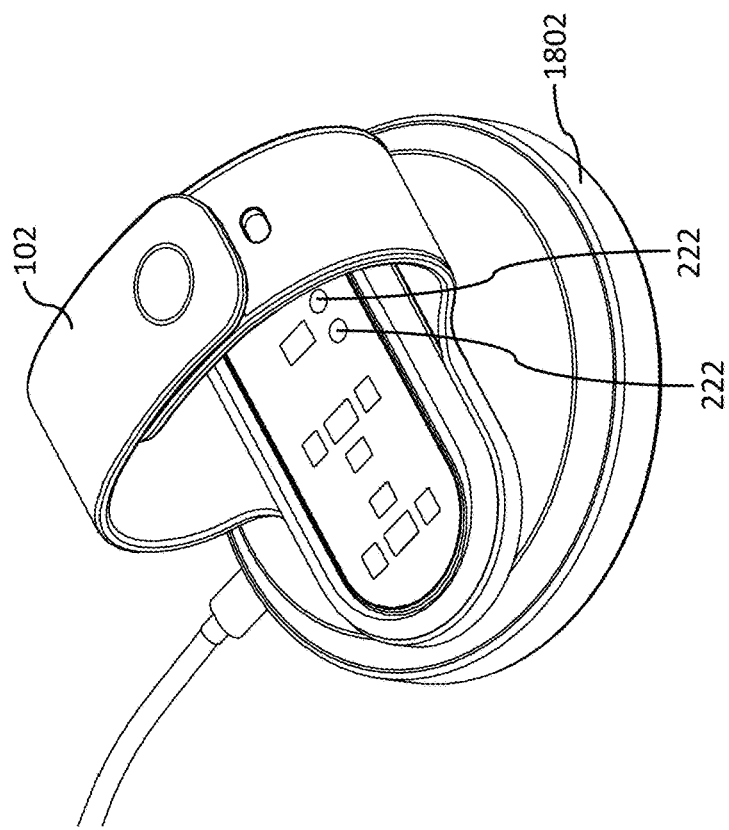

FIGS. 18A-18B illustrate the multiparameter smart wristband and the fully standalone version of the multiparameter smart wristband being charged on two different kinds of wireless charging units. In one example, the multiparameter smart wristband 102 that does not have a touchscreen display is charged upside down with its top face touching the top of Qi wirelesses charger 1802. With this charging configuration, the charging status indicator LEDs 222 are conveniently visible to the user. In another example, the multiparameter smart wristband 102 with a touchscreen display is charged with its backplate touching the top of a Qi wirelesses charger 1804. With this charging configuration, the charging status indicator LED 1806 provided on the wireless charger 1804 is conveniently visible to the user.

The specific examples provided herein relate to a multiparameter smart wristband for physiological monitoring, however, the materials, methods of application and arrangements of the invention can be varied. For example, any time periods, frequencies, and sampling rates mentioned here are variable and can be adjusted. As a further variant, the biosensors could be snugly fitted flush with the backplate. In another variant, a waterproof epoxy could be used to internally seal the PDs and/or LEDs, which would assist with water resistance.

In another variation, the custom PCB may be provided with an accelerometer chip that communicates with the microcontroller via the I2C bus. The microcontroller may acquire X, Y, Z axes data related to subject motion and posture using the accelerometer chip via the I2C bus. Since the accelerometer data may be synchronously collected with PPG waveform data, it may also be used to remove noise like motion artifacts from PPG data to increase accuracy of PR, $SpO_2$ and BP estimation. The accelerometer and related algorithms may be used to track and report motion and its intensity. Moreover, this information may also be used to remove biosensor noise that is created by motion artifacts to enhance overall measurement accuracy.

In a further variation, a thermistor or other temperature sensor could be used instead of a thermopile sensor. The voltage across the thermistor that characterizes the body temperature may be acquired by an ADC on the microcontroller. Voltage data collected from the thermistor may be used to determine the thermistor's resistance. Then, the thermistor's resistance-temperature look-up table may be used to report body temperature.

In yet a further variation, the microcontroller may time stamp acquired data and wirelessly stream this data to a base station, such as a tablet or smartphone via a Bluetooth chip which may be connected to a UART port. The microcontroller on the device may be further provided with a syncable real-time clock (RTC). All date-stamped data can be reported and stored in comma-separated value (CSV) format whereby the first column exports the time stamps while subsequent columns report values of PPG waveform and other data. Time stamping could be accomplished using the microcontroller RTC in conjunction with the base station clock.

In yet a further variation, the ECG electrode locations and numbers can vary. For example, the multiparameter smart wristband can have one ECG electrode on the bottom and two ECG electrodes on the top. In such a configuration, one ECG electrode on the backplate would contact the skin, while two ECG electrodes provided on the front face would be touched by the index finger to complete the ECG circuit.

Various programming languages such as assembly language, embedded C, C, Java, Swift, and Python may be used to develop software for accomplishing data analysis on the microcontroller and base station or external devices. The software could provide functionality such that data analysis can be done in real time on live data as well as on a post-hoc basis on stored data.

Furthermore, a structured software development kit (SDK) man be architected to enable third parties to develop software for accessing measurements from the data. The SDK documentation could outline the protocol, interface, commands, and system responses. A dynamically linked library could also be constructed and included with the SDK.

The components could be selected such that a unit cost of less than $20 (for on-patient portion excluding GPS and display) for large quantities (≥1K) is possible. Hence the device can be realized and fabricated as a low-cost yet effective multiparameter physiological monitor.

As a further variant, the smart wristband 102 of FIGS. 1 to 4 may incorporate the ECG sensors therein and further monitor ECG signals.

Figure 19:
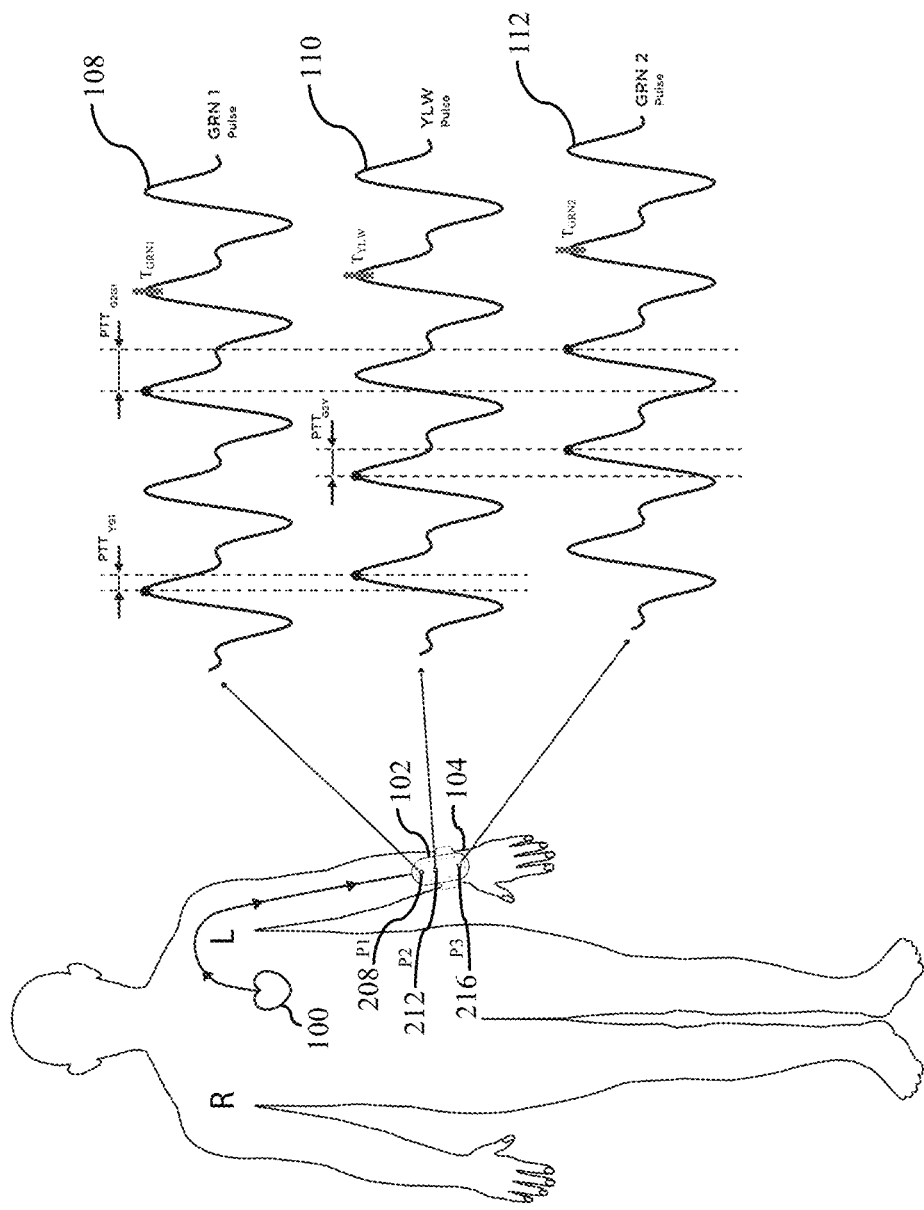
FIG. 19 illustrates how the multiparameter smart wristband of FIG. 1 accomplishes PTT and PWV measurements in accordance with an aspect of the disclosure.

FIG. 19 illustrates one embodiment of the multiparameter smart wristband for accomplishing PTT and PWV measurements. In this example, the smart wristband 102 is worn by the user on the left wrist 104 resulting in the contact of the photosensors P1 208, P2 212, P3 216 on the device backplate with the skin of the wrist. The LEDs GRN1, YLW, and GRN2 surrounding the photosensors 208, 212, 216 are not shown in FIG. 19 for brevity. As per human physiology, arterial pulse waves travel from the heart to the periphery of the body. In this embodiment, a curved line with arrows shows the travel of the arterial pulse wave from the heart 100 to the wrist 104. By virtue of the strategic placement of the photosensors 208, 212, 216 in a straight line and at optimum distances $D_{P1P2}$, $D_{P1P3}$, and $D_{P2P3}$ from each other, the multiparameter smart wristband acquires the arterial pulse wave signal from three distinctly separate locations along the wrist. This design enables the acquisition of three arterial pulse waves, i.e., GRN1 108, YLW 110, and GRN2 112, that have different pulse arrival times $T_{GRN1}$, $T_{YLW}$, and $T_{GRN2}$. In this example, the GRN1 pulse wave 108 acquired by photosensor P1 208 has the smallest pulse arrival time $T_{GRN1}$, the YLW pulse wave 110 acquired by photosensor P2 212 has a pulse arrival time $T_{YLW}$ that is greater than $T_{GRN1}$, and the GRN2 pulse wave 112 acquired by photosensor P3 216 has the largest pulse arrival time $T_{GRN2}$ (that is, $T_{GRN2} > T_{YLW} > T_{GRN1}$). These different pulse arrival times result in the acquisition of three arterial pulse waves 108, 110, and 112 that have a phase shift or time delay between each other.

In this example of FIG. 19, the GRN1 pulse wave 108 acquired by the photosensor P1 208 leads the YLW pulse wave 110 and GRN2 pulse waves 112 acquired by the photosensor P2 212 and P3 216 respectively. Additionally, the YLW pulse wave 110 acquired by the photosensor P2 212 leads the GRN2 pulse wave 112 acquired by the photosensor P3 216. The phase shift or time delay between the acquired pulse wave signals 108, 110, and 112 enables simple, seamless, and unobtrusive measurement of three pulse transit time (PTT) metrics, namely, $PTT_{YG1}=(T_{YLW}-T_{GRN1})$, $PTT_{G2Y}=(T_{GRN2}-T_{YLW})$, and $PTT_{G2G1}=(T_{GRN2}-T_{GRN1})$. Moreover, the predetermined and fixed distances $D_{P1P2}$, $D_{P1P3}$, and $D_{P2P3}$ between the photosensors P1 208, P2 212, P3 216 enable the normalized, robust, and convenient measurement of three pulse wave velocity (PWV) metrics, namely, $PWV_{YG1}=D_{P1P2}/PTT_{YG1}$, $PWV_{G2Y}=D_{P2P3}/PTT_{G2Y}$, and $PWV_{G2G1}=D_{P1P3}/PTT_{G2G1}$. The PTT and PWV metrics have been found to be critical metrics in the cuffless estimation of blood pressure. In this aspect of the disclosure, three PTT metrics and three PWV metrics namely, $PTT_{YG1}$, $PTT_{G2Y}$, $PTT_{G2G1}$, $PWV_{YG1}$, $PWV_{G2Y}$, and $PWV_{G2G1}$ are combined with other arterial pulse wave parameters for accurate cuffless estimation of blood pressure.

As will be appreciated by those of ordinary skill in the art, the solutions set forth above measure PTT and PWV using optical sensors that are unobtrusively and conveniently integrated into a device baseplate. PTT, PWV, and hence BP can be measured seamlessly without the aid of an additional ECG signal and/or auxiliary sensors (electrodes). A user is not required to touch and hold auxiliary electrodes to additionally acquire an ECG signal and then combine this ECG signal with pulse signal to measure PTT and BP. Moreover, PTT and PWV are measured using just the three or more pulse signals acquired at three or more distinct locations along the limb. Therefore, one can measure PTT, PWV, and BP on a continuous 24-7 basis (even when user is sleeping), which would not be possible if an ECG signal were also required.

Finally, since the present approach measures PTT at predetermined distances (as stipulated by the baseplate design and the placement of optical sensors therein), the PTT metric automatically characterizes the correct pulse wave velocity (PWV). This is because PWV=DISTANCE/PTT. In the present design, DISTANCE between optical sensors embedded in the baseplate is constant/predetermined. Therefore, the generated PTT metrics give direct indication or characterization of PWV, with PWV being the speed at which blood flows in the arteries and is proportional to BP. Therefore, the present method automatically provides accurate measurement of BP. Such an approach is distinguished from approaches that use an ECG signal and a pulse signal to measure PTT, where the PTT will not be enough to accurately characterize PWV and/or BP. This is because PTT measured for each user will also be affected by user height or length of user limb. In contrast, the present solution avoids this problem by integrating optical sensors at predetermined and fixed distances along the limb that naturally normalizes PTT and PWV measurements by taking user height (limb length) out of the equation.

The scope of the claims should not be limited by the preferred embodiments set forth in the examples but should be given the broadest interpretation consistent with the description as a whole.

What is claimed is:

1. A smart wristband for multiparameter physiological monitoring configured to communicate with an external device, comprising:
    a backplate;
    multiple biosensors, including at least three photoplethysmography (PPG) sensors configured to contact skin of the user in at least three separate locations;
    a microcontroller in communication with the biosensors and configured to determine multiple vital signs from data from the biosensors; and
    an accelerometer sensor, wherein the microcontroller and/or the external device acquire user activity data via the accelerometer sensor;
    wherein the at least three PPG sensors are located across a length of the backplate, separated from each other by predetermined distances, and collectively configured to measure at least three arterial pulse waveform signals each with different pulse arrival times from the at least three separate locations on the skin of the user, enabling measurement of at least three pulse transit time (PTT) and/or pulse wave velocity (PWV) signals, and wherein the microcontroller is configured to compute at least three PTT and/or PWV metrics using the different pulse arrival times and the predetermined distances, and to thereafter use the at least three PTT and/or PWV metrics to calculate at least one parameter of the user;
    wherein the microcontroller and/or the external device are configured to:
        receive the at least three arterial pulse waveform signals via the at least three PPG sensors; and
        analyze the at least three arterial pulse waveform signals to compute at least three pulse transit times (PTT), at least three pulse wave velocities (PWV), and at least three pulse amplitude metrics, and combines the at least three PTT, the at least three PWV, and the at least three pulse amplitude metrics to evaluate and report at least one non-invasive blood pressure (NIBP) parameter of the user;

analyze the at least three arterial pulse waveform signals to compute at least three peak-to-peak interval (PPI) metrics and combines the at least three PPI metrics to evaluate and report a heart rate (HR) parameter of the user;

analyze respiratory sinus arrhythmia (RSA) induced modulations in respective amplitudes of the at least three pulse waveform signals, the at least three PPI signals, and the at least three PTT signals to compute at least nine respiration rate (RR) metrics, and combines the at least nine RR metrics to evaluate and report an RR parameter of the user;

analyze the at least three arterial pulse waveform signals to compute at least two blood oxygen saturation (SpO2) metrics and combines the at least two blood SpO2 metrics to evaluate and report an SpO2 level of the user; and analyze accelerometer data from the accelerometer sensor to accurately report user activity level; and wherein the at least one parameter of the user includes the at least one NIBP parameter, the HR parameter, the RR parameter, and/or the SpO2 level of the user.

2. The smart wristband of claim 1 wherein each respective one of the at least three PPG sensors includes at least three LEDs and at least one photodiode (PD) sensor.

3. The smart wristband of claim 1 wherein the biosensors further comprise a temperature sensor, wherein the microcontroller is configured to process and aggregate data from the temperature sensor and to report body temperature.

4. The smart wristband of claim 1 wherein the biosensors further comprise at least three electrocardiogram (ECG) electrodes.

5. The smart wristband of claim 4 further comprising a top face, wherein two ECG electrodes of the at least three ECG electrodes are in the backplate, while one ECG electrode of the at least three ECG electrodes is in the top face.

6. The smart wristband of claim 1 wherein the vital signs determined by the microcontroller include HR, HRV, SpO2, NIBP, RR, body temperature and arterial pulse, along with electrocardiogram (ECG) monitoring for additional HR, HRV, and RR assessment.

7. The smart wristband of claim 1 further comprising a top face and a strap, wherein the strap includes a gasket that is sealed around the backplate, the top face, the microcontroller and the biosensors.

8. The smart wristband of claim 1 further comprising a transceiver configured for wireless communication, wherein the microcontroller is configured to utilize the transceiver to send the vital signs or data in real-time or on a post-hoc basis to an external device; and wherein the external device is configured to display data, process data, store data, and/or transmit data to other external devices.

9. The smart wristband of claim 1 further comprising a display for displaying the data and the vital signs.

10. The smart wristband of claim 1 further comprising a rechargeable battery.

11. The smart wristband of claim 8 wherein the external device and/or the microcontroller are configured to automatically detect and correct for a wrong attachment of the smart wristband on a limb of the user via identification of one or more negative pulse transit times in the at least three PTT signals obtained from the at least three PPG sensors, and if the negative pulse transit times are identified, to provide a wrong attachment alert and/or correct the one or more negative pulse transit times by multiplying the one or more negative pulse transmit times in the at least three PTT signals by −1.

12. The smart wristband of claim 1 further comprising a global positioning system (GPS) module, a memory module, and a touchscreen display, wherein the microcontroller is configured to acquire GPS data via the GPS module and analyze the GPS data to accurately report a location of the user, and wherein the microcontroller is configured to display data, store data, receive user input via the touchscreen display, and/or transmit data to one or more other external devices.

13. The smart wristband of claim 8 wherein the microcontroller and/or the external device are configured to receive an ECG waveform signal via the at least three ECG electrodes whenever two of the at least three ECG electrodes contact the skin of the user on one side of a body of the user and one of the at least three electrodes also contacts the skin of the user on the other side of the body, and wherein the microcontroller and/or the external device are configured to analyze the ECG waveform signal to report the at least one parameter of the user, the at least one parameter including an HR parameter and an HR variability (HRV) parameter of the user.

14. The smart wristband of claim 5 wherein one of the two ECG electrodes in the backplate is a driven electrode to improve an ECG signal quality.

15. The smart wristband of claim 1 further comprising a strap made of elastomeric material and configured as a single piece, such that a gasket is integrated with the strap.

16. The smart wristband of claim 8 wherein the microcontroller and/or the external device are configured to perform manual intermittent or continuous physiological monitoring as per a user specified monitoring frequency.

17. The smart wristband of claim 8 wherein the microcontroller and/or the external device are configured to generate health alerts based on the multiple vital signs from the data from the biosensors.

18. The smart wristband of claim 2 wherein the backplate comprises light barriers between all of the at least three LEDs and all of the at least one PD sensor of the at least three PPG sensors, and further comprises individual transparent lenses to isolate and encapsulate each of the at least three LEDs and the at least one PD sensor for enhancing arterial pulse waveform data quality, and for protecting the at least three LEDs and the at least one PD sensor from dust, moisture, and mechanical damage.

19. The smart wristband of claim 18 wherein the backplate is manufactured utilizing an industrial co-moulding process and formed from acrylonitrile butadiene styrene (ABS), while each of the individual transparent lenses is moulded using transparent materials.

20. The smart wristband of claim 8 wherein the microcontroller and/or the external device is configured to receive the at least three arterial pulse waveform signals via the at least three PPG sensors and utilize automatic gain control (AGC) circuitry to standardize quality and fidelity of the three arterial pulse waveform signals over all users, wherein gains of the three arterial pulse waveform signals are controlled automatically by the microcontroller and/or the external device.

21. The smart wristband of claim 8, further comprising electrocardiogram (ECG) electrodes, wherein the microcontroller and/or the external device are configured to utilize automatic gain control (AGC) circuitry to standardize quality and fidelity of an ECG signal from the ECG electrodes over all users of the smart wristband, wherein a gain of the ECG signal is controlled automatically by the microcontroller and/or the external device, or the gain is controlled manually by the user by varying a slider on a user interface.

22. The smart wristband of claim 2 wherein the microcontroller is configured to utilize pulse width modulation (PWM) technique to control the at least three LEDs of the at least three PPG sensors and synchronously read data from the at least one PD to minimize interference between unassociated LEDs and PDs and to prevent the LEDs from heating up.

23. The smart wristband of claim 1 further comprising wireless charging circuitry configured to be wirelessly charged with a wireless charging unit.

24. The smart wristband of claim 1 wherein the smart wristband is configured to be attached at various locations along limbs of the user.

25. The smart wristband of claim 1 wherein the microcontroller and/or the external device are configured to receive the at least three arterial pulse waveform signals via the at least three PPG sensors, and wherein the microcontroller and/or the external device use synchronously collected data from the accelerometer sensor to remove noise from the at least three arterial pulse waveform signals to further increase accuracy of evaluation of at least one parameter, the at least one parameter including a heart rate (HR) parameter, a heart rate variability (HRV) parameter, a respiration rate (RR) parameter, a blood oxygen saturation (SpO2) level, and/or at least one non-invasive blood pressure (NIBP) parameter of the user.

26. The smart wristband of claim 8 wherein the microcontroller and/or the external device are configured to receive the at least three arterial pulse waveform signals via the at least three PPG sensors, and wherein respective gains of the at least three arterial pulse waveform signals are controlled manually by the user by varying sliders on a user interface (UI) on the smart wristband and/or the external device that are in communication with the microcontroller that is in communication with automatic gain control (AGC) circuitry.

27. The smart wristband of claim 4, wherein the microcontroller and/or an external device are configured to receive an ECG waveform signal via the at least three ECG electrodes, and wherein the microcontroller and/or the external device use synchronously collected data from an accelerometer sensor to remove noise from the ECG waveform signal to further increase accuracy of evaluation of the at least one parameter, the at least one parameter including a heart rate (HR) parameter, a heart rate variability (HRV) parameter, and/or a respiration rate (RR) parameter of the user.

* * * * *